US011129793B2

(12) United States Patent
Betser et al.

(10) Patent No.: US 11,129,793 B2
(45) Date of Patent: *Sep. 28, 2021

(54) RETENTIVE DEVICES AND SYSTEMS FOR IN-SITU RELEASE OF PHARMACEUTICAL ACTIVE AGENTS

(71) Applicant: EPITOMEE MEDICAL LTD, Caesarea (IL)

(72) Inventors: Nir Betser, Yehud (IL); Valery Artmanov, Ashdod (IL)

(73) Assignee: EPITOMEE MEDICAL LTD, Caesarea (IL)

( * ) Notice: Subject to any disclaimer, the term of this patent is extended or adjusted under 35 U.S.C. 154(b) by 378 days.

This patent is subject to a terminal disclaimer.

(21) Appl. No.: 15/101,045

(22) PCT Filed: Dec. 4, 2014

(86) PCT No.: PCT/IL2014/051063
§ 371 (c)(1),
(2) Date: Jun. 2, 2016

(87) PCT Pub. No.: WO2015/083171
PCT Pub. Date: Jun. 11, 2015

(65) Prior Publication Data
US 2018/0250226 A1 Sep. 6, 2018

Related U.S. Application Data

(60) Provisional application No. 61/912,204, filed on Dec. 5, 2013.

(51) Int. Cl.
*A61K 9/00* (2006.01)
*A61K 9/20* (2006.01)

(52) U.S. Cl.
CPC ............ *A61K 9/0065* (2013.01); *A61K 9/205* (2013.01); *A61K 9/0004* (2013.01); *A61K 9/2086* (2013.01)

(58) Field of Classification Search
CPC .................................................. A61K 9/0065
See application file for complete search history.

(56) References Cited

U.S. PATENT DOCUMENTS

| | | |
|---|---|---|
| 2,464,693 A | 3/1949 | Kirk, Jr. et al. |
| 2,470,665 A | 5/1949 | Stiehl |
| 3,584,631 A | 6/1971 | Halter et al. |
| 3,630,114 A | 12/1971 | Bunting, Jr. et al. |
| 3,674,014 A | 7/1972 | Tillander |
| 3,774,596 A | 11/1973 | Cook |
| 3,786,813 A | 1/1974 | Michaels |
| 3,840,009 A | 10/1974 | Michaels et al. |
| 3,901,232 A | 8/1975 | Michaels et al. |
| 3,911,098 A | 10/1975 | Capozza |
| 4,027,676 A | 6/1977 | Mattei |
| 4,055,178 A | 10/1977 | Harrigan |
| 4,133,315 A | 1/1979 | Berman et al. |
| 4,140,755 A | 2/1979 | Sheth et al. |
| 4,142,526 A | 3/1979 | Zaffaroni et al. |
| 4,167,558 A | 9/1979 | Sheth et al. |
| 4,203,439 A | 5/1980 | Theeuwes |
| 4,207,890 A | 6/1980 | Mamajek et al. |
| 4,236,521 A | 12/1980 | Lauterjung |
| 4,246,893 A | 1/1981 | Berson |
| 4,308,250 A | 12/1981 | Griffin et al. |
| 4,311,146 A | 1/1982 | Wonder |
| 4,416,267 A | 11/1983 | Garren et al. |
| 4,447,227 A | 5/1984 | Kotsanis |
| 4,485,805 A | 12/1984 | Foster, Jr. |
| 4,501,264 A | 2/1985 | Rockey |
| 4,546,143 A | 10/1985 | Weil et al. |
| 4,607,618 A | 8/1986 | Angelchik |
| 4,692,152 A | 9/1987 | Emde |
| 4,694,827 A | 9/1987 | Weiner et al. |
| 4,723,547 A | 2/1988 | Kullas et al. |
| 4,739,758 A | 4/1988 | Lai et al. |
| 4,753,976 A | 6/1988 | Yoshioka et al. |
| 4,767,627 A | 8/1988 | Caldwell et al. |
| 4,790,429 A | 12/1988 | Fukushima |
| 4,812,315 A | 3/1989 | Tarabishi |
| 4,878,905 A | 11/1989 | Blass |
| 4,899,747 A | 2/1990 | Garren et al. |
| 4,925,446 A | 5/1990 | Garay et al. |
| 4,968,294 A | 11/1990 | Salama |
| 4,984,564 A | 1/1991 | Yuen |

(Continued)

FOREIGN PATENT DOCUMENTS

| | | |
|---|---|---|
| DE | 103 04 614 A1 | 8/2004 |
| EP | 0 103 481 A1 | 3/1984 |

(Continued)

OTHER PUBLICATIONS

Klucel (TM) hydroxypropylcellulose—Physical and chemical properties. Ashland 2017.*
Ratner et al., "Introduction to Materials Science", Biomaterials Science, 2004.
Japanese Office Action Translation dated Mar. 29, 2012 for Japanese Patent No. 2009-511077.
International Search Report dated Dec. 2, 2013 for PCT/IL2013/050490.
Written Opinion dated Dec. 2, 2013 for PCT/IL2013/050490, dated Dec. 7, 2014 for PCT/IL2013/050490.
International Search Report published Apr. 30, 2009 for PCT/IL06/0276 filed Mar. 1, 2006.

(Continued)

*Primary Examiner* — Hasan S Ahmed
(74) *Attorney, Agent, or Firm* — Vorys, Sater, Seymour and Pease LLP; William L. Klima

(57) ABSTRACT

Gastric retentive devices and systems including a gastric retentive element including at least one expandable compartment and a dosage form element including at least one active agent are provided. The devices and systems, as well as kits thereof are used in a method for in-situ release and delivery of the at least one active agent.

22 Claims, 16 Drawing Sheets

(56) References Cited

U.S. PATENT DOCUMENTS

| | | |
|---|---|---|
| 5,041,364 A | 8/1991 | Dickerson et al. |
| 5,084,061 A | 1/1992 | Gau et al. |
| 5,129,915 A | 7/1992 | Cantenys |
| 5,167,626 A | 12/1992 | Casper |
| 5,206,030 A | 4/1993 | Wheatley et al. |
| 5,234,454 A | 8/1993 | Bangs |
| 5,259,399 A | 11/1993 | Brown |
| 5,443,505 A | 8/1995 | Wong et al. |
| 5,520,609 A | 5/1996 | Moll et al. |
| 5,558,642 A | 9/1996 | Schweich, Jr. et al. |
| 5,649,978 A | 7/1997 | Samson |
| 5,738,629 A | 4/1998 | Moll et al. |
| 5,750,585 A | 5/1998 | Park et al. |
| 5,770,181 A | 6/1998 | Kirkland |
| 5,783,212 A | 7/1998 | Fassihi et al. |
| 5,836,871 A | 11/1998 | Wallace et al. |
| 5,893,826 A | 4/1999 | Salama |
| 5,972,369 A | 10/1999 | Roorda et al. |
| 5,989,590 A | 11/1999 | Wong et al. |
| 5,993,473 A | 11/1999 | Chan et al. |
| 6,079,871 A | 6/2000 | Jonas et al. |
| 6,120,803 A | 9/2000 | Wong et al. |
| 6,261,601 B1 | 7/2001 | Talwar et al. |
| 6,271,278 B1 | 8/2001 | Park et al. |
| 6,287,332 B1 | 9/2001 | Bolz et al. |
| 6,454,785 B2 | 9/2002 | De Hoyos Garza |
| 6,503,264 B1 | 1/2003 | Birk |
| 6,517,559 B1 | 2/2003 | O'Connell |
| 6,517,659 B1 | 2/2003 | Vanderwerf et al. |
| 6,579,301 B1 | 6/2003 | Bales et al. |
| 6,579,310 B1 | 6/2003 | Cox et al. |
| 6,605,037 B1 | 8/2003 | Moll et al. |
| 6,675,809 B2 | 1/2004 | Stack et al. |
| 6,726,920 B1 | 4/2004 | Theeuwes et al. |
| 6,733,512 B2 | 5/2004 | McGhan |
| 6,755,869 B2 | 6/2004 | Geitz |
| 6,797,283 B1 | 9/2004 | Edgren et al. |
| 6,833,488 B2 | 12/2004 | Bucevschi et al. |
| 6,845,776 B2 | 1/2005 | Stack et al. |
| 6,981,980 B2 | 1/2006 | Sampson et al. |
| 7,009,634 B2 | 3/2006 | Iddan et al. |
| 7,033,373 B2 | 4/2006 | De La Torre et al. |
| 7,052,488 B2 | 5/2006 | Uhland |
| 7,056,305 B2 | 6/2006 | Garza Alvarez |
| 7,066,945 B2 | 6/2006 | Hashiba et al. |
| 7,111,627 B2 | 9/2006 | Stack et al. |
| 7,112,186 B2 | 9/2006 | Shah |
| 7,335,210 B2 | 2/2008 | Smit |
| 7,632,291 B2 | 12/2009 | Stephens et al. |
| 7,674,396 B2 | 3/2010 | Sterling et al. |
| 7,699,863 B2 | 4/2010 | Marco et al. |
| 7,699,883 B2 | 4/2010 | Douglas |
| 7,785,291 B2 | 8/2010 | Marco et al. |
| 7,879,355 B2 | 2/2011 | Sterling et al. |
| 7,931,693 B2 | 4/2011 | Binmoeller |
| 8,267,888 B2 | 9/2012 | Marco et al. |
| 8,292,911 B2 | 10/2012 | Brister et al. |
| 8,647,358 B2 | 2/2014 | Brister et al. |
| 8,740,927 B2 | 6/2014 | Brister et al. |
| 8,845,673 B2 | 9/2014 | Marco et al. |
| 8,858,496 B2 | 10/2014 | Marco et al. |
| 8,864,784 B2 | 10/2014 | Marco et al. |
| 8,992,561 B2 | 3/2015 | Brister et al. |
| 9,119,793 B1 | 9/2015 | Bakan et al. |
| 10,507,127 B2 * | 12/2019 | Betser .................. A61F 5/0036 |
| 2003/0040804 A1 | 2/2003 | Stack et al. |
| 2003/0040808 A1 | 2/2003 | Stack et al. |
| 2003/0109935 A1 | 6/2003 | Geitz |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0212452 A1 | 11/2003 | Zadno-Azizi et al. |
| 2004/0129186 A1 | 7/2004 | Curiger |
| 2004/0143342 A1 | 7/2004 | Stack et al. |
| 2004/0186502 A1 | 9/2004 | Sampson et al. |
| 2004/0192582 A1 | 9/2004 | Burnett et al. |
| 2005/0216074 A1 | 9/2005 | Sahatjian et al. |
| 2006/0018948 A1 | 1/2006 | Guire et al. |
| 2006/0025799 A1 | 2/2006 | Basu |
| 2006/0058829 A1 | 3/2006 | Sampson et al. |
| 2006/0111632 A1 | 5/2006 | Chen |
| 2006/0111777 A1 | 5/2006 | Chen |
| 2006/0155259 A1 | 7/2006 | MacLay |
| 2006/0178726 A1 | 8/2006 | Douglas |
| 2006/0222681 A1 | 10/2006 | Richard |
| 2006/0282107 A1 | 12/2006 | Hashiba et al. |
| 2007/0078476 A1 | 4/2007 | Hull et al. |
| 2007/0100367 A1 | 5/2007 | Quijano et al. |
| 2007/0100368 A1 | 5/2007 | Quijano et al. |
| 2007/0104754 A1 | 5/2007 | Cragg et al. |
| 2007/0104755 A1 | 5/2007 | Sterling et al. |
| 2007/0106372 A1 | 5/2007 | Osborne et al. |
| 2007/0118168 A1 | 5/2007 | Lointier et al. |
| 2007/0135829 A1 | 6/2007 | Paganon |
| 2007/0224234 A1 | 9/2007 | Steckel et al. |
| 2007/0249900 A1 | 10/2007 | Wilson et al. |
| 2007/0250102 A1 | 10/2007 | Makower et al. |
| 2007/0250103 A1 | 10/2007 | Makower et al. |
| 2007/0256709 A1 | 11/2007 | Rajan et al. |
| 2007/0293716 A1 | 12/2007 | Baker et al. |
| 2008/0107732 A1 | 5/2008 | Dharmadhikari et al. |
| 2008/0206145 A1 | 8/2008 | Afargan et al. |
| 2008/0208356 A1 | 8/2008 | Stack |
| 2008/0255587 A1 | 10/2008 | Cully et al. |
| 2008/0269797 A1 | 10/2008 | Stack et al. |
| 2009/0035367 A1 | 2/2009 | Mintchev et al. |
| 2009/0098198 A1 | 4/2009 | Rousso et al. |
| 2009/0130158 A1 | 5/2009 | Dujardin et al. |
| 2009/0177215 A1 | 7/2009 | Stack et al. |
| 2009/0182424 A1 | 7/2009 | Marco |
| 2009/0299487 A1 | 12/2009 | Stack et al. |
| 2009/0304753 A1 | 12/2009 | Tsabari et al. |
| 2009/0304768 A1 | 12/2009 | Lapidot et al. |
| 2009/0318649 A1 | 12/2009 | Bucevschi |
| 2010/0129445 A1 | 5/2010 | Asmussen et al. |
| 2011/0015665 A1 | 1/2011 | Marco et al. |
| 2011/0015666 A1 | 1/2011 | Marco |
| 2011/0022072 A1 | 1/2011 | Marco et al. |
| 2011/0040318 A1 | 2/2011 | Marco et al. |
| 2011/0066175 A1 | 3/2011 | Gross |
| 2013/0218190 A1 | 8/2013 | Gaur et al. |

FOREIGN PATENT DOCUMENTS

| | | |
|---|---|---|
| JP | H03500258 A | 1/1991 |
| JP | S-24959 A | 2/1994 |
| JP | 2006522643 A | 10/2006 |
| WO | 90/00376 A1 | 1/1990 |
| WO | 99/25418 A1 | 5/1999 |
| WO | 00/25742 A1 | 5/2000 |
| WO | 02/00213 A1 | 1/2002 |
| WO | 2002/00213 A1 | 1/2002 |
| WO | 02/40081 A2 | 5/2002 |
| WO | 02/091961 A1 | 11/2002 |
| WO | 03/015745 A1 | 2/2003 |
| WO | 03/017882 A2 | 3/2003 |
| WO | 03/028477 A2 | 4/2003 |
| WO | 2004/064680 A1 | 8/2004 |
| WO | 2004/084763 A2 | 10/2004 |
| WO | 2005/018417 A2 | 3/2005 |
| WO | 2005/039458 A2 | 5/2005 |
| WO | 2005/082296 A1 | 9/2005 |
| WO | 2005/097012 A2 | 10/2005 |
| WO | 2005/101983 A1 | 11/2005 |
| WO | 2005/120363 A1 | 12/2005 |
| WO | 2006/020929 A2 | 2/2006 |
| WO | 2006/044640 A1 | 4/2006 |
| WO | 2006/047882 A1 | 5/2006 |
| WO | 2006/055839 A2 | 5/2006 |
| WO | 2006/063593 A2 | 6/2006 |
| WO | 2007/017842 A2 | 2/2007 |
| WO | 2007/083309 A2 | 7/2007 |
| WO | 2007/084724 A2 | 7/2007 |
| WO | 2007/093999 A1 | 8/2007 |

(56) References Cited

FOREIGN PATENT DOCUMENTS

| WO | 2007/109904 A1 | 10/2007 |
|---|---|---|
| WO | 2007/115169 A2 | 10/2007 |
| WO | 2007/136735 A2 | 11/2007 |
| WO | 2006/072948 A2 | 7/2009 |
| WO | 2009/086119 A2 | 7/2009 |
| WO | 2010/045477 A2 | 4/2010 |

OTHER PUBLICATIONS

Written Opinion published Mar. 20, 2009 for PCT/IL06/0276 filed Mar. 1, 2006.
International Preliminary Report on Patentability published Mar. 24, 2009 for PCT/IL06/0276 filed Mar. 1, 2006.
International Search Report published Feb. 28, 2008 for PCT/US07/11882 filed May 18, 2007 (claiming priority to U.S. Appl. No. 11/788,574).
Written Opinion published Nov. 18, 2008 for PCT/US07/11882 filed May 18, 2007 (claiming priority to U.S. Appl. No. 11/788,574).
International Preliminary Report on Patentability published Nov. 18, 2008 for PCT/US07/11882 filed May 18, 2007 (claiming priority to U.S. Appl. No. 11/788,574).
International Preliminary Examination Report dated Dec. 9, 2014 for PCT/IL2013/050490.

\* cited by examiner

Gastric retentive element (3 compartments) folded around the dosage form element

RETENTIVE DEVICES AND SYSTEMS FOR IN-SITU RELEASE OF PHARMACEUTICAL ACTIVE AGENTS

TECHNOLOGICAL FIELD

This invention relates to gastric retentive devices and systems used for in-situ release of active agents.

PRIOR ART

References considered to be relevant as background to the presently disclosed subject matter are listed below:

EP1124534 relates to a device for delaying the pylorus passage of orally administered medicament forms comprising a component which expands upon contact with the gastric juice and a polymer coat which is permeable to liquids but not to gases.

U.S. Pat. No. 3,901,232 relates to a drug delivery device for the controlled and continuous administration of a drug at a dosage unit programmed rate comprising a bioerodible hollow container housing a drug delivery device attached to a collapsed balloon.

U.S. Pat. No. 4,055,178 relates to a system composed of a drug reservoir encapsulated in a microporous compartment having pores on top and bottom surfaces. The peripheral walls of the reservoir compartment were completely sealed to prevent any physical contact of the undissolved drug with walls of the stomach.

Acknowledgement of the above references herein is not to be inferred as meaning that these are in any way relevant to the patentability of the presently disclosed subject matter.

BACKGROUND

Oral delivery of drugs is the most preferable route for drug delivery due to the ease of administration, patient compliance and flexibility in the formulations. From immediate-release (IR) to slow-release (SR), oral dosage form has really progressed during the last decades.

Drugs absorption is often unsatisfactory and highly variable among and between individuals. The reasons for that are essentially physiological and usually affected by the gastro-intestine (GI) transit of the drug, especially its gastric residence time (GRT), which appears to be one of the major causes for the overall transit time variability.

Various attempts have been recently made to develop gastro retentive delivery systems in order to address the increased interest in novel dosage forms that are retained in the stomach for prolonged and predictable period of time. Such system (for ex.) is a floating drug delivery system in the gastric fluids.

The stomach is anatomically divided into 3 regions: fundus, body, and antrum (pylorus). The proximal part made of fundus and body acts as a reservoir for undigested material, whereas the antrum is the main site for mixing motions and act as a pump for gastric emptying by propelling actions. Thus, a gastric retention device should be able to withstand the forces caused by peristaltic waves in the stomach and must resist the gastric emptying mechanism. These features are attained by the size, shape and material's structure of the gastric retention device.

Gastro retentive systems are planned to remain in the gastric region for several hours. Hence, it significantly prolongs the gastric residence time of drugs. Prolonged gastric retention modify the pharmacokinetics of the drugs by improving the bioavailability, reduces drug waste, and thus reduces side effects and increases solubility for drugs that are less soluble in the absorbent pH environment. It mostly benefits drugs that have a narrow window of absorption in the stomach and proximal small intestines.

Improved bioavailability is expected for drugs that are readily absorbed upon release in the GI tract; these drugs can be delivered ideally by slow release from the stomach. Thus, a system which is designed for longer gastric retention (gastro retentive drug delivery system; GRDDS) will extend the time that drug absorption takes place in the GI tract (mostly in the upper part of the small intestine—the preferable absorption site for many oral drugs).

Certain types of drugs and essential nutrients can benefit from using GRDDS, including those who: act locally in the stomach, primarily absorbed in the stomach, poorly soluble at an alkaline pH, has a narrow window of absorption, absorbed rapidly from the GI tract, irritating to the mucosa of the small intestine, administered two or more times a day During the past two decades, numerous oral delivery systems have been developed to act as drug reservoirs from which the active substance can be released over a defined period of time at a predetermined and controlled rate; these systems were termed as slow-release (SR) drugs. However, even though an excellent drug release profile, it is quite possible that a complete absorbance of the active ingredients at the target point will not be achieved due to insufficient GRT of the drug in the stomach.

The gastric device, described in this invention, allows for drug absorption in the upper GI tract, minimizing the amount of drug that passes through the lower GI tract. Thus it served as GRDDS, providing: greater treatment efficacy, increased treatment tolerability, reduction of side effects and the convenience of dosing.

GENERAL DESCRIPTION

When referring to "a gastric retentive element" it should be understood to include an element that provides gastric retentive properties to the system of the invention, i.e. it retains the system of the invention in the stomach for period of time beyond the typical stomach emptying time of a healthy human patient (the residence time of the system of the invention in the stomach is prolonged from the typical stomach emptying time removing digested elements from the stomach).

When referring to a "biodegradable layer", "biodegradable film" or "biodegradable multilayer" it should be understood to mean that said film/layer is degraded or film's/layer's properties are deteriorated when exposed to biological environment (i.e. in a biological system, or similar in vitro environment simulating conditions of such biological system, such as gastric tract of a treated individual When referring to "external film" it should be understood to mean any biocompatible film layer that forms the external outer surface of said compai linent. External film can be formed from at least one or a combination of non degraded and biodegradable films or layers. In some embodiments, said external film or layer can be made of portions of different types of films or layers having different characteristics (for example different rigidity) and permeability.

The term "compartment" should be understood to encompass a separate division or section having a space enclosed by said external film (in some embodiments biodegradable film or layer). Said compartment may be in any shape or form suitable for the purposes and use of the system of the invention. Furthermore, a system of the invention may include one or more of said compartments, which in some embodiments may be interconnected to one another or separated from one another. In other embodiments a system of the invention may include one or more of said compartments, which may be interconnected to one another and/or each or at least one of said compartments of said gastric retentive element is connected to said dosage form element.

The term "collapsed form" or "initial collapsed form" refers to the form of said compartment having an initial form or volume of said compartment or film of said gastric retentive element before the at least one compound capable of expanding said at least one compartment or film adsorbs stomach fluids. In this initial collapsed form the size of said gastric retentive element enables it to be encased in a swallowble capsule either as it is or in some embodiments in a folded or rolled form (either with or without said dosage form element).

The term "expanded form" refers to the shape and/or volume of said at least one compartment or film of said gastric retentive element with at least one compound capable of expanding and/or increasing the volume (and or altering the shape) of said at least one compartment or film absorbed stomach fluids. In this expanded state the shape and/or volume of said gastric retentive element increases in order to provide said gastric retentive properties (i.e. maintaining the system of the invention of both gastric retentive element and dosage form element in the stomach of a patient administered with such, for a prolonged amount of time as compared with typical stomach emptying time of a healthy human patient.

When referring to a "compound capable of expanding said at least one compartment" is meant to encompass any compound that is capable of absorbing any type of liquid(s) in contact therewith, thereby expanding the compartment (for example by increasing the volume of said compartment) to a three dimensional form having a volume higher than the initial volume of said compartment. In some embodiments said compound is a gel forming compound (for example a polymer). In some embodiments said gel forming compound may be charged (i.e. charged gel forming compound) or neutral. In other embodiments said compound is a gas forming compound.

When referring to "a dosage form element" it should be understood to comprise an element comprising at least one active agent. In some embodiments, said at least one active agent is a pharmaceutically active agent. In other embodiments said active agent is at least one commercial active agent (i.e. an active agent that is available for purchase). In some embodiments said at least one active agent is in a controlled release form. In other embodiments said at least one active agent is a poorly soluble agent. In other embodiments said at least one active agent is both in a controlled release form and is a poorly soluble agent. In other embodiments, said dosage form element is enclosed in a biodegradable enteric film (single or multilayered) wherein said film provides slow release of said at least one active agent (including delayed release, prolonged release and so forth). In other embodiments, said dosage form element is enclosed in at least one layer of film that does not alter any of said active agent properties, including for example its release profile. In other embodiment the dosage form element is a readymade, off the shelf tablet or capsule or other form of drug with no change to its properties or parameters or with very minor modifications to enable connection to the gastric retentive element or for packing the system in a swallowable capsule.

When referring to a "controlled release form" of an agent it should be understood to relate to the formulation of said agent in a manner that provides delivery of said agent in response to stimuli or time. Controlled release includes: slow release, sustained release where prolonged release is intended, pulse release, delayed release (e.g. to target different regions of the GI tract) etc. Controlled release formulations of active agents do not only prolong action but also attempt to maintain active agent levels within the therapeutic window to avoid potentially hazardous peaks in active agent concentration following administration and to maximize therapeutic efficiency.

The dosage form element may additionally contain one or more further pharmaceutical/nutritional active agents who are released upon contacted with the acidic fluid within the stomach.

When referring to "poorly soluble agents" it should be understood to include any active agent having a solubility of more than 30 parts of solvent per one part of solute at typical body temperature ranges (between about 35° C. to about 40° C.)

The present invention provides a system comprising:
- a gastric retentive element comprising at least one expandable compartment comprising at least one type of an external biodegradable and film having an collapsed form; wherein said compartment comprises at least one compound capable of expanding said at least one compartment to an expanded form; and
- a dosage form element comprising at least one active agent;

wherein said gastric retentive element and dosage form element are connected to each other.

In a further aspect the invention provides a system comprising:
- a gastric retentive element comprising at least one expandable multilayered biodegradable film comprising at least one layer comprising a biodegradable film and at least one expandable layer comprising at least one compound capable of expanding the form of said film upon contact with liquid to an expanded form; and
- a dosage form element comprising at least one active agent;

wherein said gastric retentive element and dosage form element are connected to each other.

In another one of its aspects the invention provides a system comprising:
- a gastric retentive element comprising at least one expandable compartment having an external biodegradable film having an initial collapsed form; wherein said compartment comprising at least one compound capable of expanding the form of said at least one compartment to an expanded form; and
- a dosage form element comprising at least one active agent wherein said agent is in a slow release form or is a poorly soluble agent;

wherein said gastric retentive element and dosage form element are externally connected to each other.

In another one of its aspects the invention provides a system comprising
- a gastric retentive element comprising at least one expandable compartment comprising at least one type of an external film (said external film being non-biodegradable, i.e. external non-biodegradable) having an initial collapsed form; wherein said compartment comprises at least one compound capable of expanding the form of said at least one compartment to an expanded form; and
- a dosage form element comprising at least one active agent;

wherein said gastric retentive element and dosage form element are connected to each other.

In a further aspect the invention provides a system comprising:
- a gastric retentive element comprising at least one expandable compartment comprising at least combination of external film having an initial collapsed form; wherein said compartment comprises at least one compound capable of expanding the form of said at least one compartment to an expanded form; wherein such element contains means for connection; and
- a dosage form element comprising at least one active agent;

wherein said gastric retentive element and dosage form element are connected to each other.

In some embodiments the gastric retentive element provides the system of the invention a stomach residence time of at least above 60 min.

In some embodiments, degradation or deterioration of said external biodegradable film is manifested by the reduction in one or more of film's physical properties such as for example film integrity, tensile strength and/or elasticity of said film.

In some embodiments, said external biodegradable film has a thickness of less than 70 microns. In further embodiments, said external biodegradable film has a thickness of between about 3 to about 60 microns. In yet other embodiments, said external biodegradable film has a thickness of about 3, 4, 5, 6, 7, 8, 9, 10, 15, 20, 25, 30, 35, 40, 45, 50, 55, 60 microns. In further embodiments, said external biodegradable film has a thickness of between about 10 to about 30 microns. In yet other embodiments, said external biodegradable film has a thickness of about 10, 11, 12, 13, 14, 15, 16, 17, 18, 19, 20, 21, 22, 23, 24, 25, 26, 27, 28, 29, 30 microns.

In some embodiments, said external non-biodegradable film has a thickness of less than 70 microns. In further embodiments, said external non-biodegradable film has a thickness of between about 3 to about 60 microns. In yet other embodiments, said external non-biodegradable film has a thickness of about 3, 4, 5, 6, 7, 8, 9, 10, 15, 20, 25, 30, 35, 40, 45, 50, 55, 60 microns. In further embodiments, said external non-biodegradable film has a thickness of between about 10 to about 30 microns. In yet other embodiments, said external non-biodegradable film has a thickness of about 10, 11, 12, 13, 14, 15, 16, 17, 18, 19, 20, 21, 22, 23, 24, 25, 26, 27, 28, 29, 30 microns.

In other embodiments, said external biodegradable film is a multilayered film (i.e. formed from more than one layer). In some embodiments, said multilayered film has at least two different layers. In other embodiments, said multilayered film has at least three different layers.

In yet other embodiments, said external biodegradable film is enterically degradable (i.e. its properties are deteriorated, reduction in one or more of tensile strength and/or elasticity, upon exposure to a biological system or its similar in vitro environment, for example in the intestine).

In further embodiments, said external biodegradable film is formed by any method known in the art, including but not limited to: blowing, casting, extrusion, coating, lamination and any combination thereof.

In yet further embodiments, two layers of said external biodegradable film are connected by at least one of gluing, welding, suturing, sealing, pressing or any other method known in the art to form a closed separated volume space ("pocket") enclosing said at least one gel and/or gas forming compound, defined above and below as the compartment.

In some embodiment, said external biodegradable film of a compartment of a device of the invention is foldable in a manner that enables its enclosure in a swallowable capsule (i.e. when folding the external biodegradable film or said compartment made of film, said film is not brittle or suffers any breakage).

Thus, as defined herein above and below, a capsule of a device of the invention, i.e. a swallowable size capsule, encases said at least one compartment in a folded or non-expanded form. In some embodiments, said capsule may be replaced by easily dissolved outer coating such as for example sugar, agar, edible polymer coating and so forth.

One embodiment of an orally administrable device according to the invention includes a gastric retentive element externally connected to a dosage form element encased within a gastric degradable swallowable capsule. The external connection between the two elements may formed by a continuous contact of their surfaces or non-continues contact through connectors such as (for example) absorbable medical suture.

The gastric retentive element contains one expandable compartment, or numerous expandable compartments connected or unconnected, comprising at least one type of an external biodegradable film having the envelope for at least one swellable compound capable of expanding the form (by for example increasing the volume of the compartment), or expandable multilayered film comprising at least one layer of biodegradable film and at least one expandable layer of compound(s) capable of increasing and/or expanding the volume and/or shape and form of the compai linent. Such inflation occurs when the compartment(s) contacted with a liquid substance, i.e. fluids in the stomach.

In some embodiments, said expansion is performed in about 30 minutes from outer swallowable capsule dissolution. In another embodiment, said expansion is performed in about 20, 15, 10, 5, 3, 2, 1 minutes after outer swallowable capsule dissolution.

In some embodiments the dosage form element comprises at least one commercial active agent (i.e. an active agent that is available for purchase) from the manufacturer and can be of a slow-release (SR) form or an immediate-release (IR) form or any combinations thereof.

In some embodiments the dosage form element is a ready made, off the shelf tablet or capsule or other form of drug with no change to any of its parameters or properties (other than minute modifications to allow connection to the gastric retentive element or for packing the system in a swallowable capsule).

In some embodiments, at least a part of an IR form of an active agent in said dosage form element may be endowed with at least SR properties by the use of a wrapping layer enclosing said dosage form element with said external biodegradable film which may be the same or different from the external film of said gastric retentive element.

In some embodiments, said dosage form element may have multiple release properties of said active agent. For example the active agent in said dosage form element is formulated in dual formulation phases so that at least a part of said active agent in said dosage form element is released in the stomach of said patient and at least another part of said active agent is formulated so that it releases once the dosage element passes through the pylorus to the deudendum.

In some other embodiments said dosage form element comprises at least one active agent so that said active agent characteristics (such as for example solubility, release, pharmacokinetics, pharmacodynamic properties and so forth) are not affected by said dosage form element (for example in embodiments where said element comprises a film). Although contact with the gastric retentive element, the dosage form element is intact in terms of the active agent behavior (such as the profile release or the agent properties) except the retaining time in the stomach.

Prolonged retention of the active agent within the stomach is achieved by its carry upon the gastric retentive element. When said device is swallowed and reaches the stomach, the external capsule disintegrates and the compartment(s) are expanded creating a 3-dimensional structure. This structure is of a size that prevents its passage through the pylorus and emptying from the stomach, keeping the dosage form element for longer time within the stomach. The integrity of the structure, in addition to the tensile strength of the external envelope film, enables the compartment(s) to withstand high forces caused by the dynamic activity of the stomach fluid for between about 1 h to about 30 days. Then, the compartment's structure loses its rigidity (by for example disintegration of external film, leakage of compound that increases the volume of said compartment or gel shrinking) and the compartments volume declines.

In some embodiments device retains in the stomach for about 2, 3, 4, 6, 8, 12, 16, 20, 24 hours or for whole day or for overnight after administration. In further embodiments device is retained in the stomach for about 1, 2, 3, 4, 5, 6, 7, 8, 9, 10, 14, 21, 28 days after administration.

In some embodiments said gastric retentive element comprises at least one expandable compartment comprising at least one type of an external film having an initial volume; wherein said compartment comprises at least one compound capable of increasing the volume of said at least one compartment to an expanded volume when exposed to a liquid substance, such as for example liquid within the stomach.

In other embodiments said gastric retentive element comprises at least one expandable multilayered film comprising at least layer comprising a film and at least one expandable layer comprising at least one compound capable of increasing the volume of said film to an expanded volume upon contact with liquid.

When reaching the stomach said compartment or film of said gastric retentive element is expanded from its initial volume to an expanded volume upon wetting of said at least one compound by fluids in the stomach. Wetting of said at least one compound by stomach fluids is achievable by the constructions and/or the properties of said external biodegradable film or expandable multilayered film. Upon increasing its volume, said gastric retentive element reaches an expanded volume that allows for the gastric retention of the system in the stomach.

In some embodiments, when said gastric retention element is expanded to its expanded volume it floats, or is buoyed on or in the fluids of the stomach.

In some other embodiments, when said gastric retention element is expanded to its expanded volume it will have gravity higher than the gravity of fluid in the stomach of said patient administered with a system of the invention. By this embodiment, said gastric retentive element occupies and/or tends to move to the lower part of said stomach (sinks to the lower part of the stomach, i.e. closer to the pylorous). This embodiment is achieved when said gastric retentive element comprises components that have gravity higher than the gravity of fluid in the stomach of a patient. Such components, for example might have higher gravity than the gravity of said stomach fluid upon their contact with said stomach fluids.

In other embodiments, when said gastric retention element is expanded to its expanded volume it is adhered to the inner wall of said stomach. Under such embodiments, said adhesion to said inner stomach wall is achieved by using at least one type of said external film having at least a part made of a material capable of adhering to said inner stomach wall such as for example polyethylene oxide.

In some further embodiments, when said gastric retention element is expanded to its expanded state said volume and/or shape of said element does not allow for said system of the invention to move through the gastric sphincters (either lower or upper sphincters) as long as said volume and/or shape of said gastric retention element is maintained.

In some embodiments the gastric retention element is floating or buoyant in the gastric fluid being connected to the dosage form element having the weight of between about 0.1-2000 mg, in other embodiments the weight is of between about 200-1500 mg.

In some embodiments the gastric retentive element maintains its expanded shape for 2, 3, 4, 6, 8, 12, 16, 20, 24 hours or for whole day or for overnight after administration. In further embodiments the gastric retentive element maintains its expanded shape for 1, 2, 3, 4, 5, 6, 7, 8, 9, 10, 14, 21, 28 days after administration.

In some embodiments, when said gastric retention element is expanded to its expanded volume it floats or is buoyed on or in the fluids of the stomach. The mechanical properties of the expanded element allows the element to keep its shape for the predetermined time.

It is to be noted that the property of buoyancy of the retentive element of the invention is provided by an upward force exerted by the fluid in which it is immersed in, that opposes the weight of an immersed object, in this case, the gastric retentive element. In a column of fluid, pressure increases with depth as a result of the weight of the overlying fluid. Thus a column of fluid, or an object submerged in the fluid, experiences greater pressure at the bottom of the column than at the top. This difference in pressure results in a net force that tends to accelerate an object upwards. The magnitude of that force is proportional to the difference in the pressure between the top and the bottom of the column, and is also equivalent to the weight of the fluid that would otherwise occupy the column, i.e. the displaced fluid. For this reason, an object whose density is greater than that of the fluid in which it is submerged tends to sink. If the object is either less dense than the liquid or is shaped appropriately (as in a boat), the force can keep the object afloat.

In some other embodiments, said dosage form element has the dimensions that does not allow for said system of the invention to move through the gastric sphincters (either lower or upper sphincters, such as for example the pylorus) until full or partial depletion of said active agent from said dosage form element.

It is noted that the diameter of the pylorus varies between individuals from about 1 to about 4 cm, averaging about 2 cm. In some embodiments expanding gastric retention dosage form expands to have the diameters that causes gastric retention.

In some embodiments, said at least one compartment has a total filling volume of at least 1 $cm^3$. In further embodiments, said compartment has a filling volume of about 1, 2, 3, 4, 5, 6, 7, 8, 9, 10, 15, 20, 25, 30, 35, 40, 45, 50, 55, 60, 65, 70, 75, 80, 85, 90, 95, 100 $cm^3$. In other embodiments, said compartment has a filling volume of about 3 $cm^3$ to about 100 $cm^3$. In other embodiments, said compartment has a filling volume of between about 3 $cm^3$ to about 70 $cm^3$. In yet other embodiments, said compartment has a filling volume of between about 3 cm³ to about 10 cm³.

In other embodiments, said single compartment has dimensions of between about 15 to about 95 mm in max external length and between about 5 to 35 mm in max external width. In yet other embodiments, said compartment has a max external elongation of about 15, 16, 17, 18, 19, 20, 25, 35, 45, 55, 65, 75, 85, 95 mm and max external wideness of about 5, 6, 7, 8, 9, 10, 15, 20, 25, 30, 35 mm. In yet some other embodiments, said compartment has dimensions of between about 50 to about 75 mm in max external length and between about 12 to about 25 mm in max external width. In yet further embodiments, said compartment has a max external elongation of about 50, 55, 60, 65, 70, 75 mm and max external wideness of about 12, 13, 14, 15, 16, 17, 18, 19, 20, 21, 22, 23, 24, 25 mm.

In some other embodiments, said device of the invention has a mass of between about 1 to about 65 gr (grams) at the expanded state in gastric fluids or simulated gastric fluids (defined at 37° C. for 1 hour). In yet other embodiments, said device of the invention has a mass of about 1, 2, 3, 4, 5, 6, 7, 8, 9, 10, 11, 12, 13, 14, 15, 20, 25, 30, 35, 40, 45, 50, 55, 60, 65 gr at the expanded state. In further embodiments, said device of the invention has a mass of between about 8 to about 35 gr at the expanded state. In yet further embodiments, said device of the invention has a mass of about 5, 6, 7, 8, 9, 10, 11, 12, 13, 14, 15, 20, 25, 30, 35 gr at the expanded state.

In some further embodiments said inflation of said gastric retentive element is delayed, i.e. the inflation of the gastric retentive element (whether a compartment or a film) can be delayed in the stomach and occur only upon a predetermined amount of time after reaching the stomach of a patient in need thereof. The delayed reaction can be controlled by several mechanisms, which basically operated when gastric fluid comes in contact with the gastric retentive element, as follows: (i) using different compositions forming the biodegradable film of the element having different porosity (ii) perforating said film with at least one aperture (iii) using a combination of compounds capable of increasing the volume of said at least one compartment or film to an expanded volume.

In some embodiment said gastric retentive element maintains the expanded retentive structure by sequentially activating expansion of compartments. In yet further embodiments, said device of the invention total compartment mass (additive) is between about 1 to about 65 gr.

In some embodiments, said active agent is selected from (but not limited to) the following group consisting of gastro retentive pharmaceutical agents: clarithromycin, cimetidine, ciproflaxin, oxarbazepine, gabapentin, pregabalin, trimetazidine, feropenem, acyclovir, carbidopa, levodopa, methyldopa, alpha-methyldopa, verapamil, propranolol, carvedilol, atenolol, albuterol, pirbuterol, nifedipine, nimodipine, acyclovir, valacyclovir, nicardipine, amlodipine, prazosin, guanabenz, allopurinol, metoprolol, oxprenolol, baclofen, clozapine, sumatriptan, benazepril, enalapril, lisinopril, captopril, quinapril, metformin, sitagliptin, glipizide, duloxetine, moxipril, norfloxacin, indolapril, diltiazem, methyl phenydate, olindapril, retinapril, spirapril, cilazapril, perindopril, gemfibrozil, phenytoin, ramipril, zofenopril, fosinopril, nitrofurantoin, valacyclovir, azithromycin, inosine, AZT, didanosine, pranobex, tribavirin, vidarabine, simvastatin, pravastatin, atorvastatin, lovastatin, selegiline, midazolam, lithium carbonate, allopurinol, cimetidine, ranitidine, famotidine, nizatidine, bifentidine, nifentidine, tramadol hydrochloride, venlafaxine, roxatidine, omeprazole, esomeprasole, lansoprazole, pantoprazole, antacids such as magnesium carbonate, aluminum carbonate, calcium carbonate or citrate, bismuth subsalicylate, bismuth subcitrate, aluminum hydroxide, magnesium oxide and sucralfate, carbenoloxalone, misoprostol, pirenzepine, telenzepine, bismuth salts, metronidazole, ciprofloxacin, clarithromycin, amoxicillin, cephalexin, zaleplon, methylnaltrexone, furosemide, topiramide, tetracycline, didanosine, the anti-tumor drug such: 5-fluorouracil, doxorubicin, mitomycin, semustine, cisplatin, etoposide, methotrexate, hydrochlorothiazide, orlistat and pharmaceutically acceptable salts, esters or prodrugs thereof.

In some embodiments, said active agent is selected from (but not limited to) the following group consisting nutritional agents vitamins (such ascorbic acid, folic acid, vitamin E), riboflavin, niacin, essential nutrients, probiotics agents, gastric beneficial microorganisms and any combinations thereof.

In some embodiments, said at least one pharmaceutically active agent in a slow release form is selected from a group consisting of: Metoprolol Succinate ER (Toprol XL), Ciprofloxacin (Cipro XR—Tablets extended release (XR): 500 and 1000 mg), Carbamazepine (Tegretol®-XR extended-release tablets 100 mg, 200 mg, 400 mg), Metformin (Glucophage-Tablets (extended release): 500, 750, and 1000 mg, Acyclovir (poorly soluble) (Zovirax-Tablets: 400 and 800 mg), Cardiodopa/Levodopa (Sinemet, Sinemet CR: 10/100 mg, 25/100 mg, 50/200 mg), Cardiodopa/levodopa/Entacapone (Stalevo: 37.5/150/200 mg, 50/200/200 mg) and any combinations thereof.

Solubility is defined as a maximum quantity of solute that can dissolve in a certain quantity of solvent or quantity of solution at a specified temperature. In some embodiments said poorly soluble agents include any pharmaceutically active agent having a solubility of between 30 to 100 parts of solvent per one part of solute at typical body temperature ranges (i.e. sparingly soluble). In other embodiments said poorly soluble agents include any pharmaceutically active agent having a solubility of between 100 to 1000 parts of solvent per one part of solute at typical body temperature ranges (i.e. slightly soluble). In further embodiments said poorly soluble agents include any pharmaceutically active agent having a solubility of between 1000 to 10,000 parts of solvent per one part of solute at typical body temperature ranges (i.e. very slightly soluble). In yet further embodiments said poorly soluble agents include any pharmaceutically active agent having a solubility of more than 10,000 parts of solvent per one part of solute at typical body temperature ranges (i.e. insoluble).

In some embodiments said dosage form element further comprises at least one of essential nutrient, probiotic agent, gastric beneficial microorganisms and diagnostic agents.

In some embodiments of the invention, said gastric retentive element and dosage form element are externally connected to each other. The term "externally connected" is meant to encompass a connection that is formed between the said elements by one point of attachment or more, however said connection is external to the element itself and is non-continuous (i.e. discontinuous and interrupted, not forming a continuous surface between said elements).

In other embodiments of the invention, said gastric retentive element and dosage form element are connected to each other using an external over-layer (similar or different than the film and layers of each element). The term "connected" is meant to encompass a connection that is formed between the said elements by one or more over layers forming a continuous layer, however keeping each element separate from each other. It should be understood that the dosage form element contains an active agent that has a weight of between about 200-2000 mg.

In some embodiments said external connection is at least one direct connection point between the out surfaces of said elements. In other embodiments, said external connection is at least one connection linking element between the outer surfaces of said elements. In some embodiments said linking element is a biodegradable film (the same or different than said biodegradable film above) or an absorbable medical suture (non-limiting examples include: Vicryl Rapide™ produced by ETHICON or Dexon™ produced by COVIDIEN).

In some embodiments said dosage form element comprises at least one active agent, wherein said agent is encased within a compartment having at least one type of an external film (in some embodiments a biodegradable film which might be the same or different from said film of said gastric retentive element).

In some embodiments, said compartment encasing said dosage from element will alter the bioavailability profile of said active agent. In some other embodiments, said compartment encasing said dosage from element will not alter the bioavailability profile of said active agent.

In some embodiments, said compartment encasing said dosage from element includes one compound capable of altering the bioavailability of said agent. In some embodiments, said compartment encasing said dosage from element further includes at least one compound capable of increasing its volume.

In some embodiments said dosage from element is connected to said gastric retentive element by at least one external link (such as for example a thread made of biocompatible compounds). In some other embodiments said linking thread has the length to allow said dosage form element to move through the pylorus to the upper deudendum part, while the gastric retentive element is maintained in the stomach.

In another embodiment, said dosage form element is connected to a gastric retentive element further comprises at least one active agent and at least one expandable compartment having an external biodegradable film having an initial volume; wherein said compartment comprises at least one compound capable of increasing the volume of said at least one compartment.

In yet further embodiments, at least two said compartments of said gastric retentive element form a structure, or multi-structure construction containing repeatable (the same) or unrepeatable (different) of said structures. Structures type may be selected from the following non-limiting list including: ring, rod, octet, triangle, square, pentagon, hexagon or any other polygonal shape. The element is built with the appropriate mechanical characteristics that allows it to maintain its shape and structure for a predefined time.

In some embodiments said compartment is formed by at least one type of biodegradable film. In other embodiments, said compartment is formed by at least two types of biodegradable films. When said compartment is formed by at least two types of biodegradable films, such films may from a homogeneous or non-homogeneous surface.

In a further embodiments said gastric retentive element further comprises at least one active agent. Thus, in such embodiments, at least one further active agent is comprised in said gastric retentive element of said system of the invention.

In another embodiment, said dosage form element is connected to a gastric retentive element further comprises at least one active agent at least one expandable compartment having an external biodegradable film having an initial volume; wherein said compartment comprises at least one compound capable of increasing the volume of said at least one compartment.

In some embodiments the gel matrix can be cross-linked. The term includes compounds from any source, being a natural source (wherein said compound forms a biopolymer), a synthetic source or a semi-synthetic source, and any combinations thereof.

Without being bound by theory, the molecular weight of the gel forming compounds and the degree of cross-linking within the gel matrix are the major factors that dictate the gel's consistency (e.g. hardness or rigidity) and contributes to its rheological properties (e.g. viscosity). Non-limiting examples of gel forming compounds include hydrogels, organogels, xerogels, and any combinations thereof.

In some embodiments, said at least one gel forming compound is selected from: (i) a biopolymer source such as for example: Gelatin, Alginate, Chitosan, Dextran, Collagen, Hyaluronic-acid, Polyglutamic-acid, and Elastin; (ii) semi-synthetic or synthetic polymer source, such as for example: Calcium polycarbophil, Acrylamides, Styrene maleic anhydride, Polyethylene oxide, Polyacrylic-acid, Polyethylene glycol, Carboxy Methyl Cellulose, Poly Vinyl Pyrrolidone, Sodium Polyacrylate, Hydroxypropyl Methyl Cellulose, and any combinations thereof. In further embodiments, said at least one gel forming compound is a combination of at least one compound from the list of group-i and at least one compound from the list of group-ii.

In some embodiments at least one gel forming compound of a composition of the invention may be further cross-linked.

In some other embodiments, said at least one gel forming compound has a swelling ratio of about 10 to 100 times-fold (w/w) (under conditions of: gastric pH at 37° C. for 1 hour).

The term "swelling ratio" represents the expansion extent of said gel forming compound between the state prior to adsorbing liquid (i.e. dry or semi dry form) and after adsorbing the maximal possible amount of liquid. Said swelling ratio is defined by weight-based and calculated according to the following equation: [wet weight−(dry weight*k)]/[(dry weight*k)]. The constant k represents the forming materials that are left after expansion of the device under the above conditions.

Gel forming compounds have the following advantages: (1) a much faster swelling degree that would be more useful for stomach specific delivery systems (2) unchanged molecular entity of the materials thus no alteration regarding the complex toxicity is expected. Gel forming compounds further provide rigid consistency to the compartment after absoption of liquid (refers herein to water or gastric fluid) that prevents to some degree leakage of the filler under bursting, rupturing and/or puncturing of the envelop-film. Moreover, gel forming compounds which are cross-linked reach higher rigidity than non-cross linked compounds.

In some embodiments said composition comprises at least one charged gel forming compound and at least one compound having an opposite charge, constructing a PEC (Poly Electrolyte Complex) formation upon liquid adsorption. In some embodiments, said at least one charged forming compound is selected from the following list: Polyvinyl acetate diethyl amino acetate (AEA), Poly-lysine, Chitosan, Polymethacrylate (Eudragit E), Poly-arginine. In other embodiments, said opposite charged compound is selected from the following list: Gelatin, Hyaluronic-acid, Sodium Poly-acrylate, Heparin, Poly acrylic-acid (Carbomer), Alginate, Pectin, Carboxy methyl cellulose. In some embodiments, at least one of said charged forming compound and/or at least one of said opposite charged compound, within said PEC, might be a gel forming compound and can be used for said device purposes.

In further embodiments, said at least one compound having an opposite charge, is added in excess (i.e. above the analytical amount of said charged gel forming compound). It is stipulated that addition of said at least one compound having an opposite charge in excess results in a large osmotic swelling force in addition to charge repulsion effect which together support in a massive fluid intake.

In some embodiments the ratio between said at least one charged gel forming compound and said at least one compound having an opposite charge is between about 99:1 to about 50:50. In other embodiments said ratio is about 99:1, 95:5, 90:10, 85:15, 80:20, 75:25, 70:30, 65:35, 60:40, 55:45, 50:50.

In some further embodiments said at least one charged gel forming compound is at least one SAP (Super Absorbent Polymer) allowing the swelling.

The term "Super Absorbent Polymer" is meant to encompass a number of cross-linked polymers, all have the basic ability to absorb massive quantities of liquids, such as water (or liquids containing water). They absorb water using the process of osmosis (water molecules pass through a barrier from one side to the other). When water passes the barrier (herein the external biodegradable film) and comes in contact with the polymer, the polymer swells. Non limiting examples of SAP are: Poly ethylene glycol (PEG), Poly glutamic-acid (PGA), Poly-acrylamid, Alginic-acid, Dextran, Poly acrylic-acid, Ethylene maleic, Carboxymethylcellulose (CMC), Pullulan, Starch, and any combinations thereof.

In yet further embodiments, said composition comprises at least one said charged forming compound acting as a linker within the PEC that forms a rigid gel within said at least one compartment that is non-leachable (i.e. the gel does not leach out of said compartment even upon break of said external biodegradable film).

Is some embodiments, said composition comprising said gel forming compound of said at least one compartment is being gradually degraded and disintegrated after it absorbs liquid and forms said gel. It is noted that degradation of said gel could be achieved by any process including: mechanical degradation (such as gastric/intestine pulses), chemical degradation (such as acidic/basic pH) or biological degradation (such as enzymatic activity).

In some embodiments upon formation of a gel in said at least one compartment, said compartment reaches a rigidity that measured by holding maximal internal pressure of 0.15-1.50 atm. In other embodiments, said compartment reaches rigidity under pressure of 0.50-1.00 atm. In further embodiments, said compartment reaches rigidity under pressure of 0.20-0.50 atm.

In some embodiments, the formation of a gel from said at least one gel forming compound in said at least one compartment may occur at pH≤6. In other embodiments the formation of a gel from said at least one gel forming compound in said at least one compartment may occur at a pH of about 2, 3, 4, 5 or 6.

In other embodiments, the formation of a gel from said gel forming compound in said at least one compartment occurs under surrounding (i.e. liquid surrounding said compartment) conductivity of between about 5 to about 35 mS. In other embodiments the formation of a gel may occur at conductivity of about: 5, 10, 15, 20, 25, 30, 35 mS.

In some embodiments, at least one said gel forming compound is in the form of a powder. In other embodiments, at least one said gel forming compound is in the form of a liquid.

In some embodiments, at least one said gel forming compound is in the form of a film (referred as "gel-film" in some embodiments). Under these embodiments, said gel-film comprises film forming compounds (other than said gel forming compound listed above), such as for example: hydrophilic film-former, hydrophobic film former, non-degradable film former, degradable film former, plasticizers, binders, super absorbent polymers, co-polymers, osmognates, and so forth. Said gel-film may be formed by any method known in the art, including but not limited to: blowing, casting, extrusion, coating, lamination and any combination thereof.

In some embodiments, said gel-film comprises at least two layers. In further embodiments, at least one layer of said gel-film is composed of at least one gel forming compound. In other embodiments, said gel-film may be formed from at least two layers, each of which comprises independently at least one gel forming compound, which may be the same or different. In further embodiments, a device of the invention may comprise at least two (the same or different) gel films.

In some embodiments, said gel-film has a thickness of less than 1500 microns. In further embodiments, said gel-film has a thickness of between about 50 to about 300 microns. In yet other embodiments, said gel-film has a thickness of about 50, 60, 70, 80, 90, 100, 110, 120, 130, 140, 150, 160, 170, 180, 190, 200, 210, 220, 230, 240, 250, 300, 400, 500, 600, 700, 800, 900, 1000, 1100, 1200, 1300, 1400, 1500 microns. In further embodiments, said gel-film has a thickness of between about 160 to about 250 microns. In yet other embodiments, said gel-film has a thickness of about 160, 170, 180, 190, 200, 210, 220, 230, 240, 250 microns.

In some embodiments, said compartment may further comprise at least one gas forming compound. In other embodiments, at least one said gas and gel forming compounds are formulated into a single film (or a film having a single layer) (in some embodiments said film is a single layer film. In other embodiments said film is a multi layered film, i.e. at least two layers).

In some embodiments, said compartment may further comprise at least one gas forming compound. In other embodiments, at least one said gas and gel forming compounds are formulated into a single film (or a film having a single layer) (in some embodiments said film is a single layer film. In other embodiments said film is a multi layered film, i.e. at least two layers).

The term "gas forming compound" is meant to encompass any compound that is capable of absorbing any type of liquid(s) in contact therewith, thereby producing gas. In some embodiments the produced gas swells the compartment to form a three dimensional structure.

Non-limiting examples of gas forming compound are Sodium Carbonate, Sodium Bicarbonate, Ascorbic Acid, Fumaric Acid, Glutamic Acid, Sodium Acid Pyrophosphate, Citric Acid, Malic Acid, Tartaric Acid, Calcium Carbonate, Potassium Bicarbonate, and any combinations thereof.

In some embodiments, said external biodegradable film comprises at least one of a binder, plasticizer, pore-former, emulsifier, film-former, and any combinations thereof.

In some embodiments, said gel film comprises at least one additive selected from of a binder, plasticizer, gel-former, solvent, osmognate, and any combinations thereof.

Non limiting examples of a suitable hydrophilic film-former additives include: Polyvinylpyrrolidone (Plasdone, Kollidon), Polyvinyl alcohol, Kollicoat IR, Hydroxypropyl cellulose (Klucel), Methylcellulose, and any combinations thereof.

Non limiting examples of a suitable plasticizer include: Glycerin, Triethyl citrate (TEC), Triacetine (TRI), Tributyl citrate (TBC), Acetyl tributyl citrate (ATBC), Acetyl triethyl citrate, Polyethylene glycol (PEG 400-6000), Oleic acid, Castor oil, Diethyl phthalate (DEP), Propylene glycol, Dibutyl sebacate (DBS), Acetylated fatty-acid glycerides (Myvacet), Glycerol Mono Stearate (GMS), and any combinations thereof.

Non limiting examples of a suitable emulsifier include: Polysorbate, Triton X-100, Span, Glycerin, Glycerol Mono Stearate (GMS), and any combination thereof.

Non limiting examples of a suitable osmognate include: Sucrose, Dextrose, Lactose, Fructose, NaCl, KCl, and any combinations thereof.

Non limiting examples of compounds suitable for forming said external biodegradable film include: Hypromellose Phthalate, Cellulose-Acetate-Phthalate, Hypromellose Acetate Succinate, Cellulose-Acetate, Ethyl-Cellulose, Poly-Methyl-Metacrylate, Poly-Ethyl-Acrylate, Poly-Vinyl-Acrylate-Phathalate, Poly-Vinyl-Acetate, Shellac, Carboxymethyl ethylcellulose (CMEC), and any combinations thereof.

Non limiting examples of a suitable solvent include: Ethanol, Methanol, Isopropanol, Acetone, Chloroform, Ethyl Acetate, and any combinations thereof.

In some embodiments, said gel forming film is part of at least one expandable multilayered biodegradable film comprising: at least one layer of external biodegradable film, and at least one expandable layer of at least one compound that capable to increase the volume of said film upon contact with liquid to an expanded volume forming at least one expandable compartment.

In some other embodiments, at least one layer of said multilayered film is enterically degradable (i.e. when said film is exposed to natural pH (in biological system or similar in vitro environment, i.e. in the intestine) at least one of its properties deteriorates by reduction in one or more of tensile strength and/or elasticity).

In a further embodiment, said system of the invention is being encased in a gastric degradable swallowable capsule. In some embodiments, said gastric degradable swallowable capsule has a size of about elongated 000 or 000 capsule or less (i.e. outer diameter of about 9.97 mm or less, height or locked length of about 30.0 mm or less and actual volume of about 1.68 ml or less). Table 1 below provides non-limiting capsule sizes suitable for the invention.

In some embodiments said compartment and/or dosage form has means to interconnect between them.

TABLE 1

Non-limiting capsule sizes

| Capsule size | Outer Diameter (mm) | Height or Locked Length (mm) | Actual Volume (ml) |
|---|---|---|---|
| Elongated 000 | 9.97 | 30.0 | 1.68 |
| 000 | 9.97 | 26.14 | 1.37 |
| 00 | 8.53 | 23.30 | 0.95 |
| 0 | 7.65 | 21.70 | 0.68 |
| 1 | 6.91 | 19.40 | 0.50 |
| 2 | 6.35 | 18.00 | 0.37 |
| 3 | 5.82 | 15.90 | 0.30 |
| 4 | 5.31 | 14.30 | 0.21 |
| 5 | 4.91 | 11.10 | 0.13 |

Non-limiting examples of gastric degradable capsules include the following manufacturers: Capsugel, Qualicap, ACG, Embo, Orpac, Chemcaps, Eei capsules and Golden capsules.

Said capsule is capable of encasing within its volume void, said at least one compartment of a device of the invention so as to completely enclose said at least one compartment within said closed capsule. Encasing said at least one compartment into said capsule may be performed by any method known in the art including: folding, rolling, creasing, collapsing, squeezing, pressing, wringing, cutting and so forth. Upon encasing said at least one compartment into said capsule, said compartment is defined to be in its closed or compressed form.

In other embodiments, said at least one compound capable of increasing the volume of said at least one compartment forms one of the layers of said biodegradable film. In some embodiments said at least one compound capable of increasing the volume of said at least one compartment or film is a hydrogel. In some further embodiments, said film comprising said hydrogel is composed of two layers pre-casted upon a support film (such as for example MYLAR-A®). The support film enables the casting of the first-layer (PVOH or Klucel or Kollicoat-IR® or Methocel or Povidone) without an adhesive material, while it provides elasticity and protection for the second casted-layer during manufacturing and storage of the final device since the support film is actually detached and removed in the course of the device preparation. However, the second casted-layer Luquasorb(FP800):Lactose:PEG:Kollidon or Carbopol:Chitosan:PEG:Klucel or Poly-Acrylic-Acid:Chitosan:PEG:Klucel or SephadexG-100:Lactose:TEC:Klucel) contains: particles suspension (rather than a polymer solution) of polymers that compose a swellable gel-matrix, plasticizer and binder to assemble the particles into a suspension.

In some embodiments, said expanded film has a thickness of less than 400 microns.

In other embodiments, said expanded film has a thickness of between about 150 to 350 microns. In some other embodiments said expandable film has a thickness of between about 150 to 190 microns.

In other embodiments, said external biodegradable film has a thickness of less than 400 microns.

In further embodiments, said external biodegradable film has a thickness of between about 3 to 60 microns. In other embodiments said external biodegradable film has a thickness of between about 10 to 25 microns.

In other embodiments, said film is a multilayered film, i.e. said film comprises more than one layer of biodegradable material. In some embodiments said more than one layer comprises the same or different biodegradable material.

In some embodiments, said film has at least two different layers. In other embodiments, said film has at least three different layers.

In some other embodiments, at least one layer of said multilayered film is enterically degradable (i.e. when said film is exposed to natural pH (in biological system or similar in vitro environment, i.e. in the intestine) at least one of its properties deteriorates by reduction in one or more of tensile strength and/or elasticity).

In further embodiments, said film comprises at least one mechanical or chemically formed aperture.

In further embodiments, said at least one compound capable of increasing the volume of said at least one compartment is selected from a gel forming compound, a gas forming compound, a foam forming compound, a compound capable of swelling a compound capable of adsorbing liquid and any combinations thereof.

In other embodiments, said gel forming compound is selected from Gelatin, Alginates, Chitosan, Amylose, Collagen, Sodium Poly-Acrylate, modified Starch, Carbopol, Polyethylen Oxide, Methocel, Metholose, Elastin, Hyaluronic acid, Sephadex, Poly(L-lysine), Poly (D,L-Argenin), Poly (σ-guanidine-α-aminobutyric acid), Polymethacrylates, and any combinations thereof.

In other embodiments, said gas forming compound is an effervescent compound or combination of at least two effervescent compounds such as for example an organic acid and an alkali carbonate. In some embodiments said alkali carbonate is selected from a group consisting of sodium carbonate, calcium carbonate, sodium bicarbonate and potassium bicarbonate and any combinations thereof. In further embodiments said organic acid is selected from the group consisting of malic acid, fumaric acid, tartaric acid, citric acid, ascorbic acid, glutamic acid and sodium acid pyrophosphate and any combinations thereof.

In further embodiments, said system of the invention comprising at least two compartments each independently having an external biodegradable film, each independently enclosing at least one compound capable of increasing the volume of said compartment.

In some embodiments, said at least one compartment has a total filling volume of at least 1 $cm^3$. In some other embodiments, said at least one compartment has a total filling volume of between about 1 $cm^3$-50 $cm^3$, i.e. 1, 2, 3, 4, 5, 10, 15, 20, 25, 30, 35, 40, 45, 50 $cm^3$ filling volume.

In another embodiment, upon reaching the stomach said external biodegradable film of said at least one compartment allows for the penetration of liquid into said compartment, thereby at least partially increasing its volume.

In some embodiments, said pharmaceutically active agent is selected from the group consisting of clarithromycin, cimetidine, ciproflaxin, oxarbazepine, gabapentin, pregabalin, trimetazidine, feropenem, acyclovir, carbidopa, levodopa, methyldopa, verapamil, propranolol, carvedilol, atenolol, albuterol, pirbuterol, nifedipine, nimodipine, nicardipine, amlodipine, prazosin, guanabenz, allopurinol, metoprolol, oxprenolol, baclofen, sumatriptan, benazepril, enalapril, lisinopril, captopril, quinapril, metformin, moxipril, indolapril, olindapril, retinapril, spirapril, cilazapril, perindopril, ramipril, zofenopril, fosinopril, nitrofurantoin, valacyclovir, azithromycin, inosine, didanosine, pranobex, tribavirin, vidarabine, simvastatin, pravastatin, atorvastatin, lovastatin, selegiline, midazolam, lithium carbonate, cimetidine, ranitidine, famotidine, nizatidine, bifentidine, nifentidine, roxatidine, omeprazole, lansoprazole, pantoprazole, antacids such as magnesium carbonate, aluminum carbonate, aluminum hydroxide, magnesium oxide and sucralfate, carbenoloxalone, misoprostol, pirenzepine, telenzepine, bismuth salts, metronidazole, ciprofloxacin, clarithromycin, amoxicillin, cephalexin, ascorbic acid, folic acid, vitamin E, niacin, furosemide, topiramide, hydrochlorothiazide, orlistat and pharmaceutically acceptable salts, esters or prodrugs thereof.

In further embodiments said at least one pharmaceutically active agent is in a controlled release formulation. In some further embodiments, said controlled release formulation is a gastric controlled release formulation.

In other embodiments, said pharmaceutically active agent has a dosage of at least 200 mg. In other embodiments, said pharmaceutically active agent has a dosage of between 50 mg-2000 mg. In some embodiments, said pharmaceutically active agent is selected from the group consisting of Metformin (Glucophage, Glumetza), Cimetidine (Tagamet), Acyclovir (Zovirax), Clarithromycin (Biaxin), Cardiodopa/Levodopa (Sinemet, Sinemet CR), Cardiodopa/levodopa/Entacapone (Stalevo) and any combinations thereof.

In another one of its aspects the invention provides a method of gastrically delivering a active agent to a patient comprising: administering to said patient a system of the invention.

In a further aspect the invention provides a kit comprising a system according to the invention and instructions for use thereof.

In some embodiments of a kit of the invention, it further comprises means for delivering the device into a stomach of a patient.

In yet further embodiments, said kit of the invention further comprises a degradation formulation which when contacted with said system in a stomach of a patient structurally degrades the system.

In some embodiments said degradation formulation comprises antacids which directly neutralize acidity like sodium and potassium bicarbonates (such as Alka-Seltzer, Brioschi).

It should be understood that the retentive time of said system of the invention in the stomach of said patient can be designed depending on the retentive needs by using the specific combination of film, expanding method and structure to allow for various combination according to various specific requirements.

Since the stomachs conditions (such as temperature, pH, salinity, etc) are altered under different patient conditions (health condition, food consumption during the times of the day and so forth), said system of the invention is designed to fit each of said conditions of the stomach.

In some embodiments, the system of the invention is designed (both from the point of view of the elements it is made of, film, linking elements and so forth, and from the point of view of the 3D structure of said elements) to achieve its effect during night time, when the pH of the stomach is lower than during the day and the peristaltic stomach waves are stronger.

The device of the invention allows the administration of an off the shelf tablet that is readymade, without altering any of its properties and connecting it to a gastric retentive device, thus providing a prolonged stomach retention of said drug in the stomach for more effective treatment with said drug, having less side effect than in regular administration of said drug without the retentive element.

In some embodiments said gastric retentive element is connected to a device such as for example, a sensing device, a diagnostic device, a therapeutic device, a camera, a pH sensor, a pressure sensor, a liquid volume sensor, a nutrient detector, an electric pulse device, a radiation device, a chemotherapy device, an electrical stimulation, a magnetic stimulation device and any combinations thereof.

DETAILED DESCRIPTION OF EMBODIMENTS

The following will relate to specific embodiments of a system of the invention and its uses for the purpose of the invention.

FIG. 1 depicts a stomach (100) of a patient having stomach fluids (101), the esophagus (102), the pylorus (103) and the duodenum (104). The stomach has an upper part (fundus 105), the body of the stomach (106), and the lower part of the stomach (antrum 107). FIG. 1 depicts a system of the invention (200) inside stomach of the patient, floating on the stomach fluids in the upper part of the stomach. Said system of the invention is shown to have a gastric retentive element (201) in its expanded state (for example in this embodiment the compartment of said element is expanded with gas forming compounds) and a dosage form element (202).

FIG. 2 depicts a stomach of a patient comprising a device of the invention (300) inside stomach of the patient, sinking in the stomach fluids to the lower part of the stomach. Said system of the invention is shown to have a gastric retentive element (301) in its expanded state (for example in this embodiment the compartment of said element is expanded with gel forming compounds, having a gravity higher than the gravity of stomach liquids) and a dosage form element (302).

FIG. 3 depicts a stomach of a patient comprising a device of the invention (400), having a gastric retentive element containing three compartments (401, 402, 403) in the expanded form and a dosage form element (404) comprising a commercially available drug in its final form (405) in a closed continuous film (406).

FIG. 4 depicts a stomach of a patient comprising a device of the invention (400), having a gastric retentive element containing three compartments (401, 402, 403) in the expanded form and a dosage form element (404) comprising a commercially available drug in its final form (405) in a closed continuous film (406) wherein said elements are connected via an external connecting link (made for example from a suture thread).

FIG. 5 depicts a stomach of a patient comprising a device of the invention (500), having a gastric retentive element containing three compartments (501, 502, 503) in the expanded form and a dosage form element (504) comprising a commercially available drug in its final form (505) in a closed net (506).

FIG. 6 depicts an example of a compartment of a gastric retentive element (top view) in its initial volume (dry form before expanding) (600), showing the top external layer of biodegradable film (601), and encasing a compound capable of increasing the volume of said element (602). The peripheral marked area (603) describes the area wherein the top film layer and the bottom film layer (not shown) of said compartment are joint together.

FIG. 7 depicts a cross section of the compartment of FIG. 5, wherein said compartment of a gastric retentive element is in its initial volume (dry form before expanding) (600), showing the top external layer of biodegradable film (601), and lower external layer of biodegradable film (604), encasing a compound capable of increasing the volume of said element. The peripheral marked area (603) describes the area wherein the top film layer and the bottom film layer (not shown) of said compartment are joint together.

FIG. 8 is a segment of FIG. 6 and FIG. 7 showing the top (601) and bottom (604) external film layer and a gel film layer (602).

FIG. 9 depicts a cross section of the compartment of a gastric retentive element of the invention, wherein said compartment of a gastric retentive element is in its initial volume (dry form before expanding) (600), showing different top external layer of biodegradable film (601), and lower external layer of biodegradable film (604), encasing a compound capable of increasing the volume of said element. The peripheral marked area (603) describes the area wherein the top film layer and the bottom film layer (not shown) of said compartment are joint together.

Figure 1:
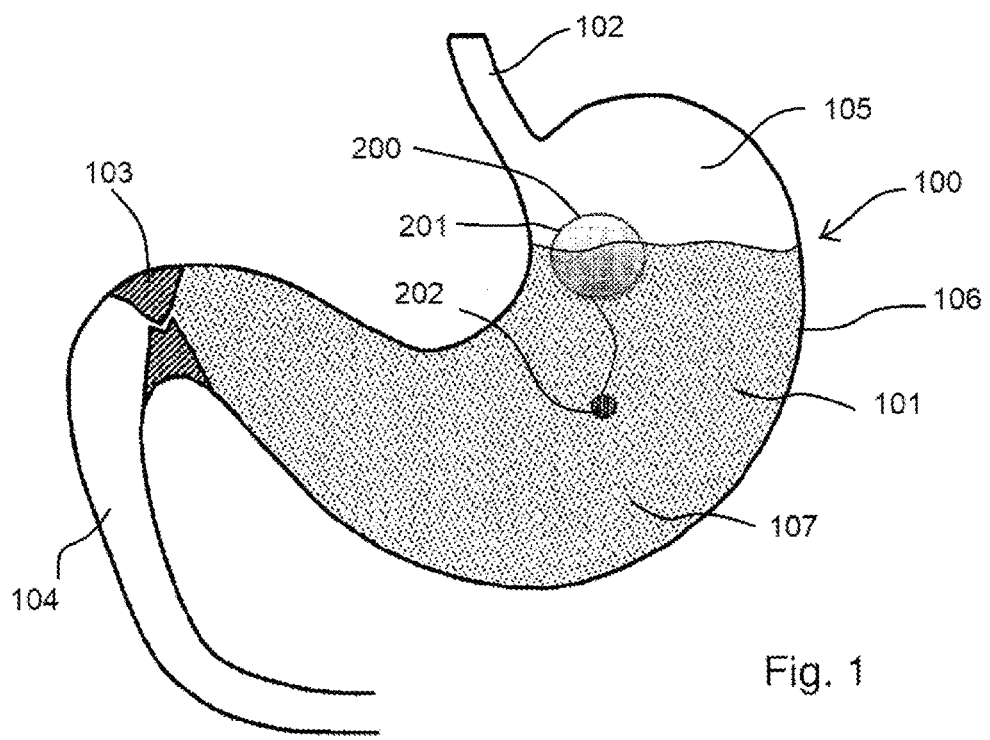
Figure 2:
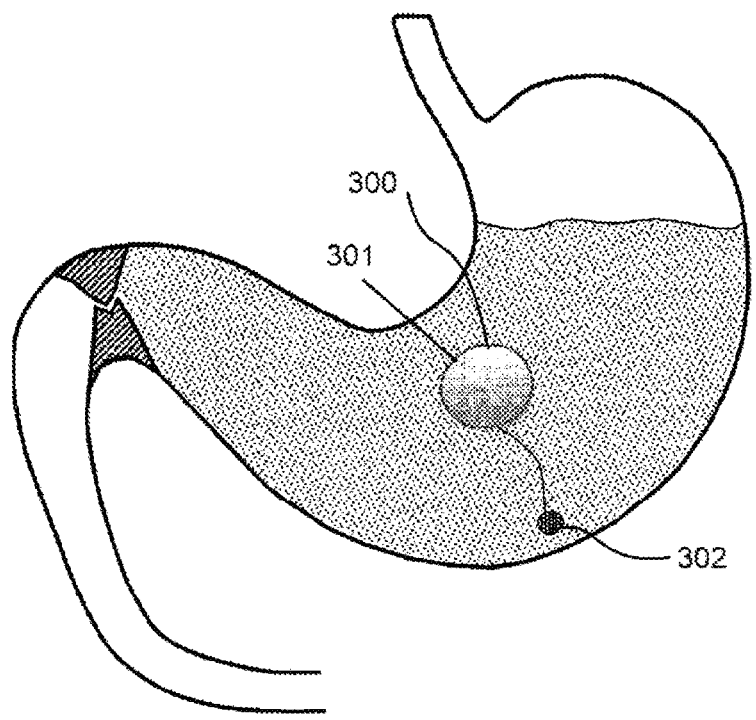
Figure 3:
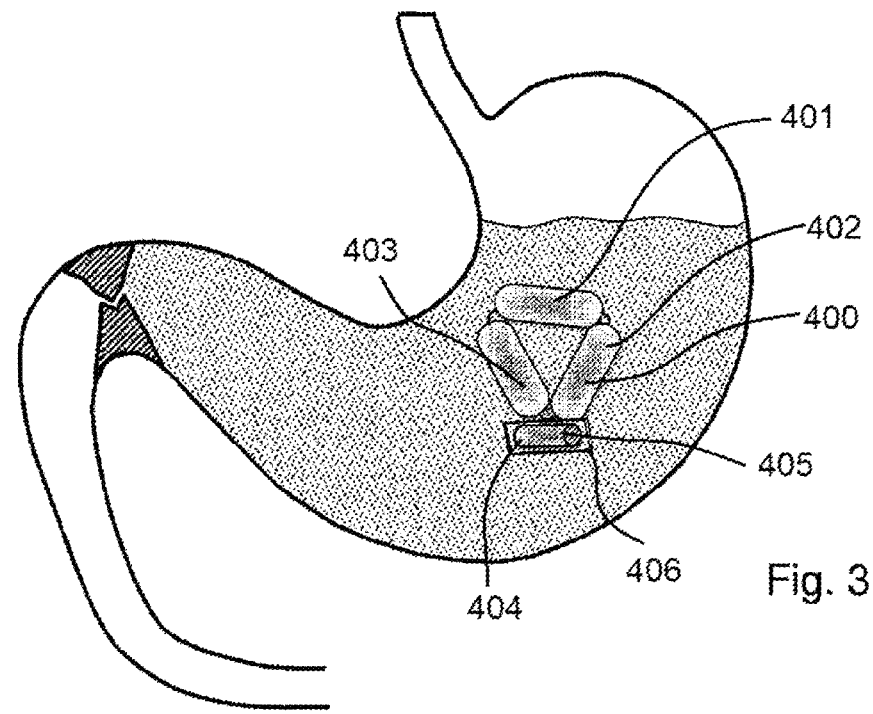
Figure 4:
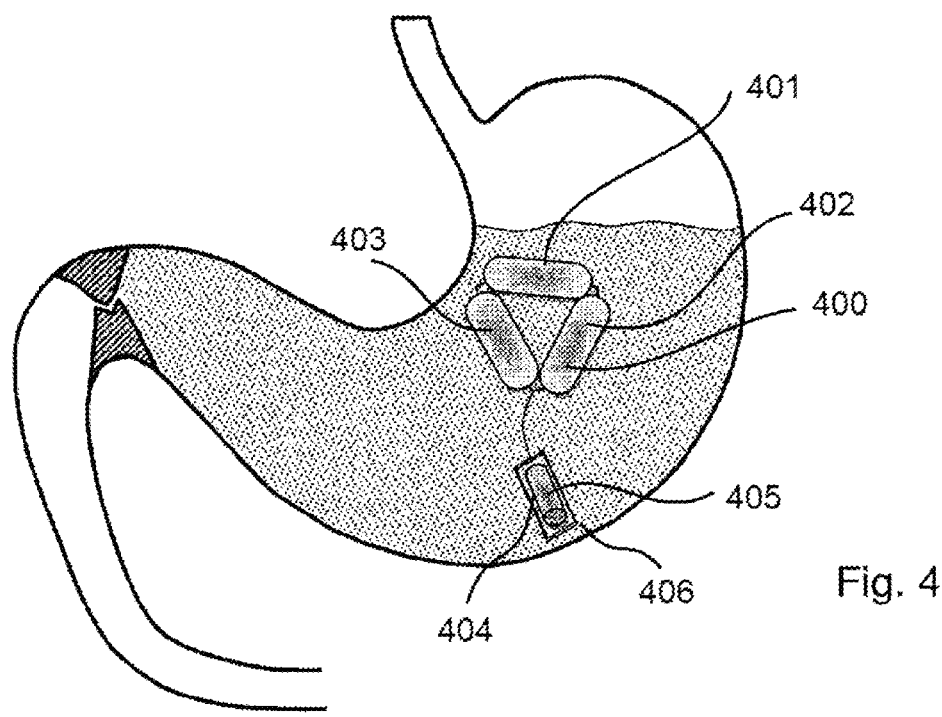
Figure 5:
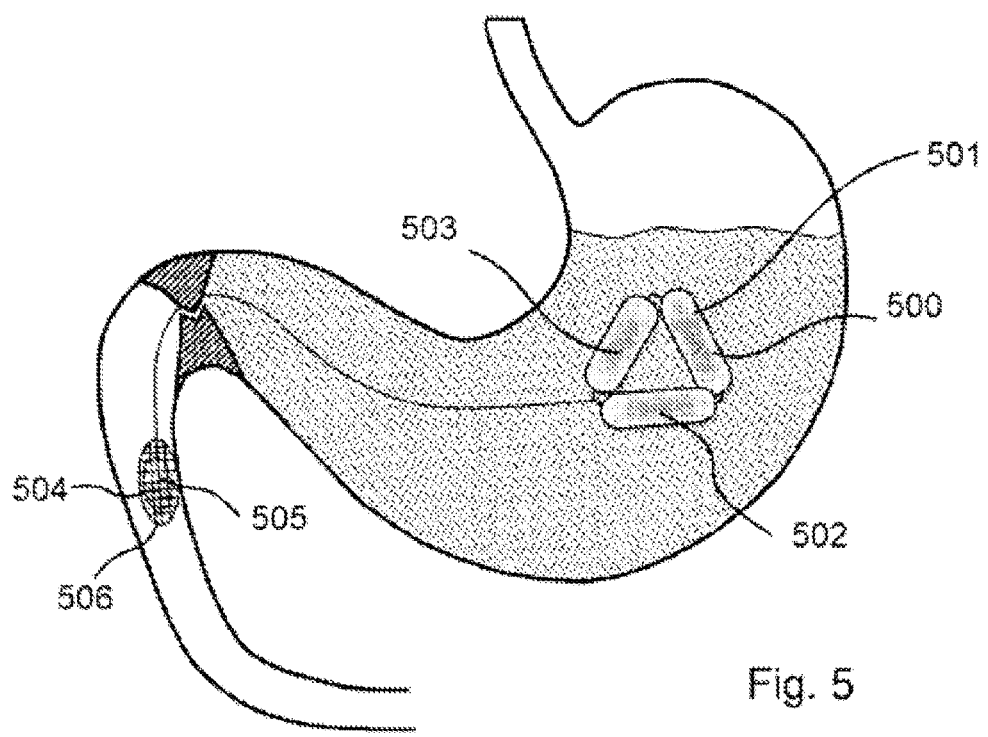
Figure 6:
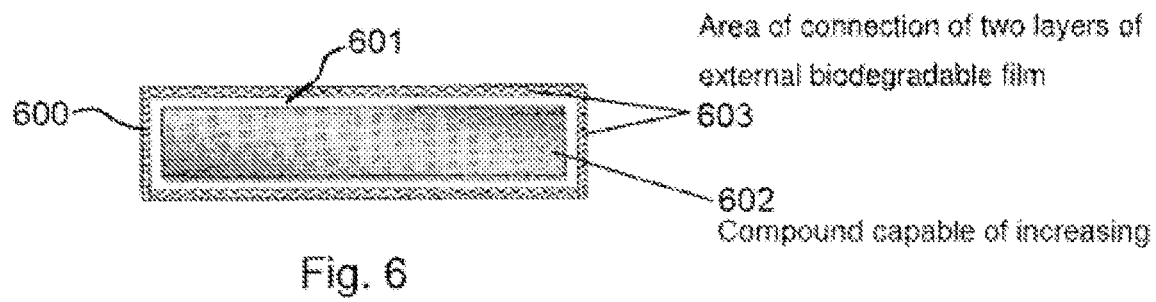
Figure 7:
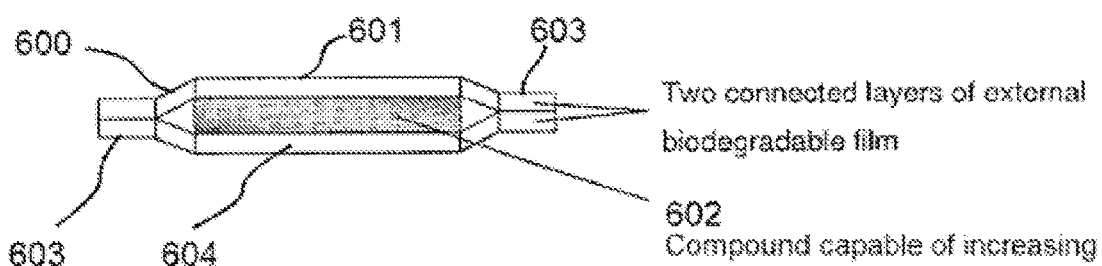
Figure 8:
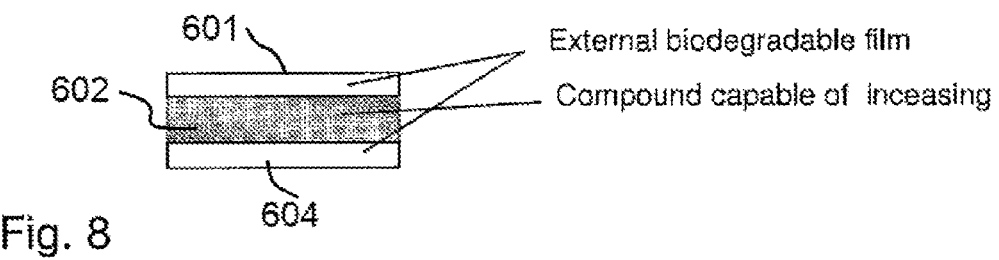
Figure 9:
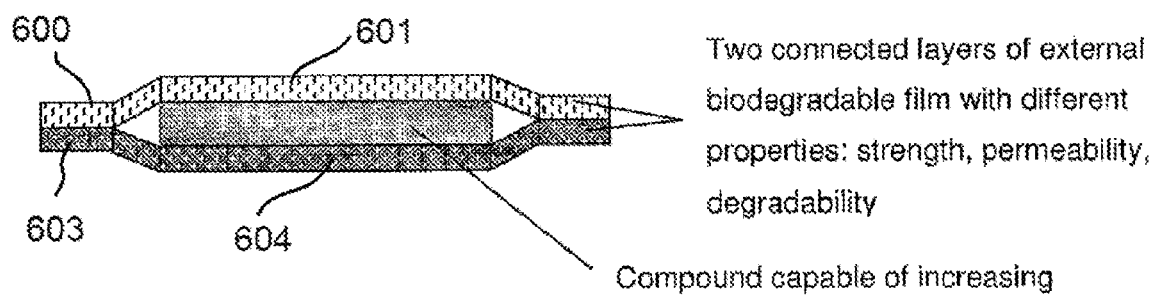
Figure 10:
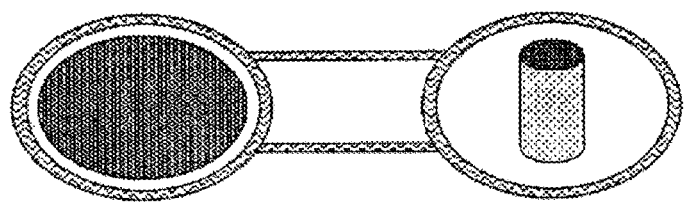
FIG. 10 depicts an embodiment of a device of the invention wherein two continuous films are holding in-between them in separate segments said two elements, i.e. at least one compound capable of expanding the compartment and a drug. The interconnecting film is made of separate segments.
Figure 11:
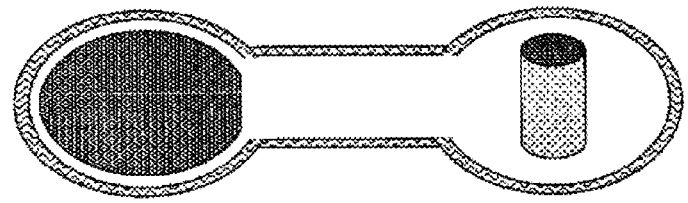
FIG. 11 depicts an embodiment of a device of the invention wherein two continuous films are holding in-between them in separate segments said two elements, i.e. at least one compound capable of expanding the compartment and a drug. The interconnecting film is made of a continuous segment of said external layers.
Figure 12:
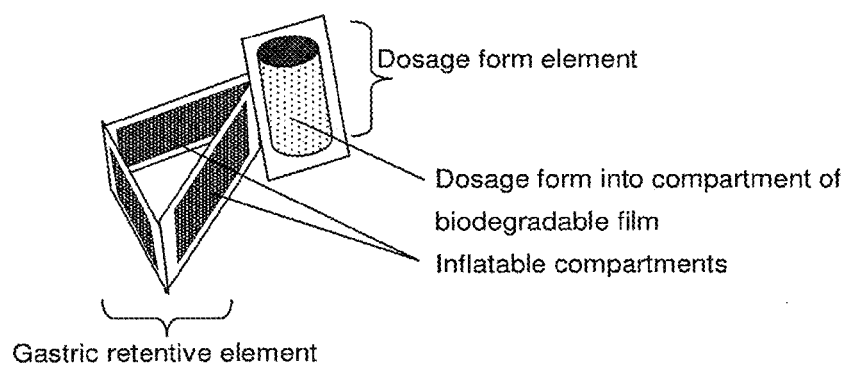
FIG. 12 depicts a device of the invention having a dosage form element connected to three gastric retentive compartments.
Figure 13:
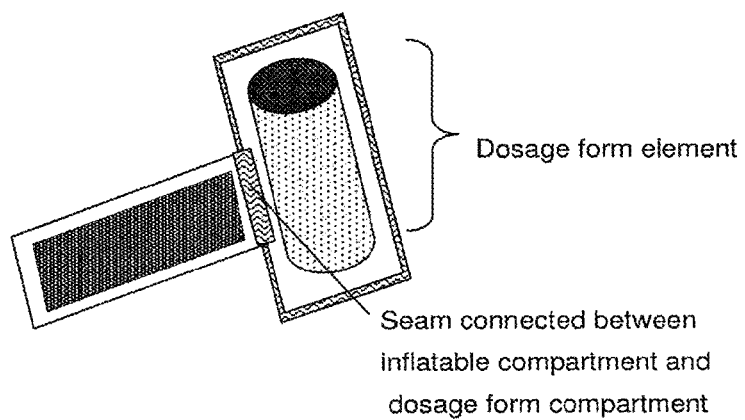
FIG. 13 depicts a device of the invention having a dosage form element connected with a seam to a single gastric retentive compartment.
Figure 14:
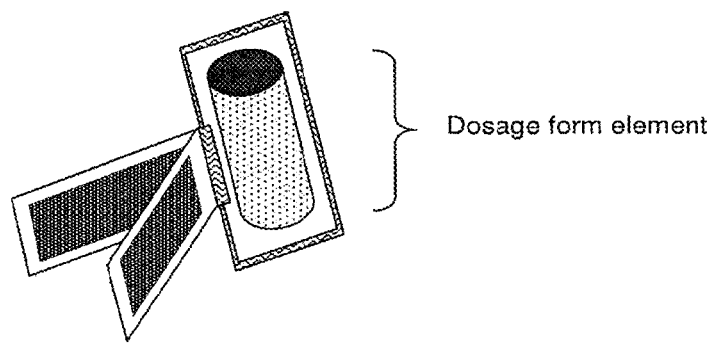
FIG. 14 and FIG. 15 depicts a device of the invention having a dosage form element connected with a seam to two gastric retentive compartments (one the same side of dosage form element in FIG. 14; and on opposite sides of dosage form element in FIG. 15).
Figure 15:
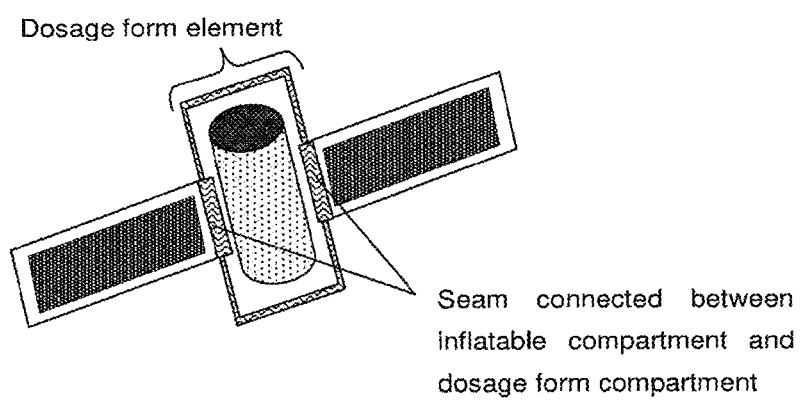
Figure 16:
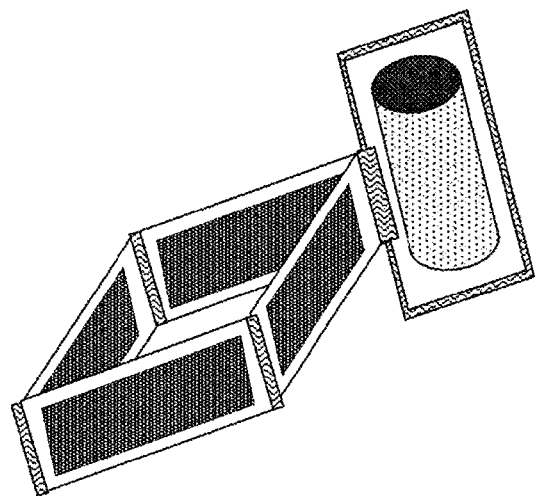
FIG. 16, FIG. 17, FIG. 18 and FIG. 19 depict a device of the invention having a dosage form element connected with a seam to four gastric retentive compartments.
Figure 17:
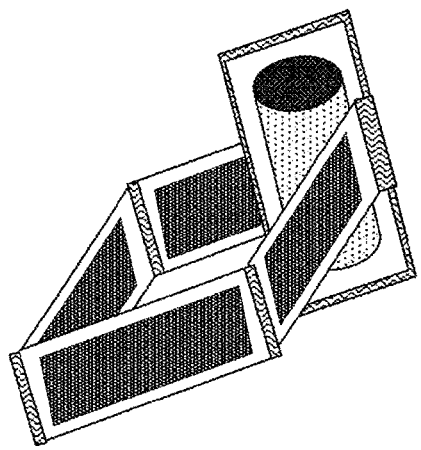
Figure 18:
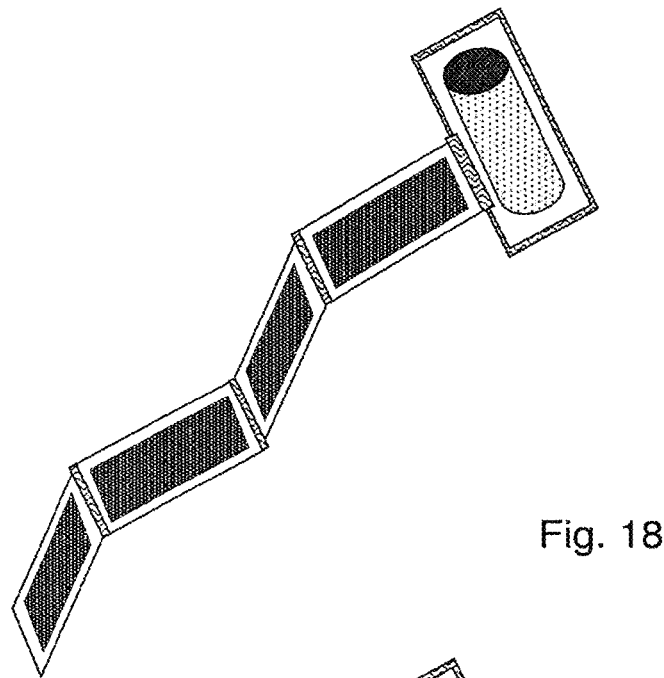
Figure 19:
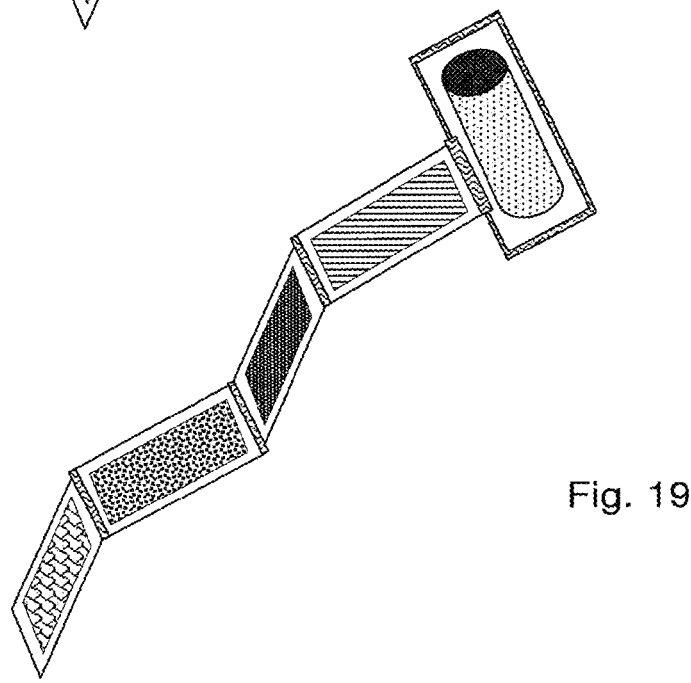
Figure 20:
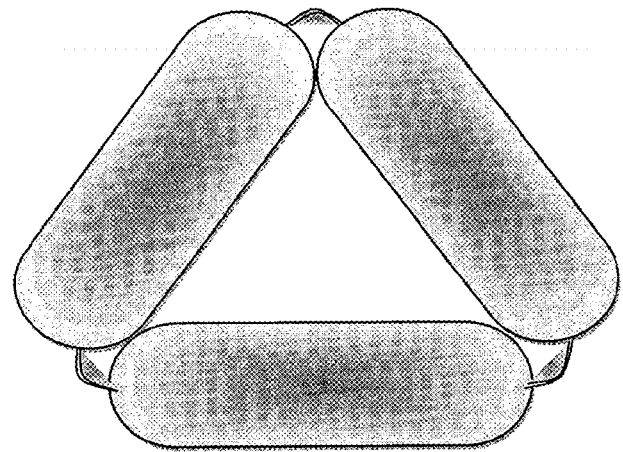
FIG. 20 depicts a gastric retentive element of a device of the invention having three compartments interconnected between them in their wet expanded form.
Figure 21:
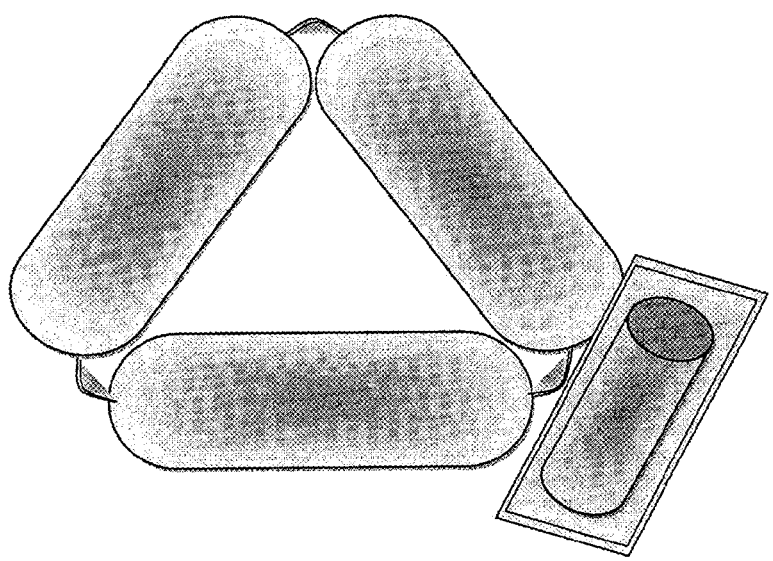
FIG. 21 depicts a gastric retentive element of a device of the invention having three compartments interconnected between them in their wet expanded form connected through a seam to a dosage form element wherein said drug is encased in a film layer.
Figure 22:
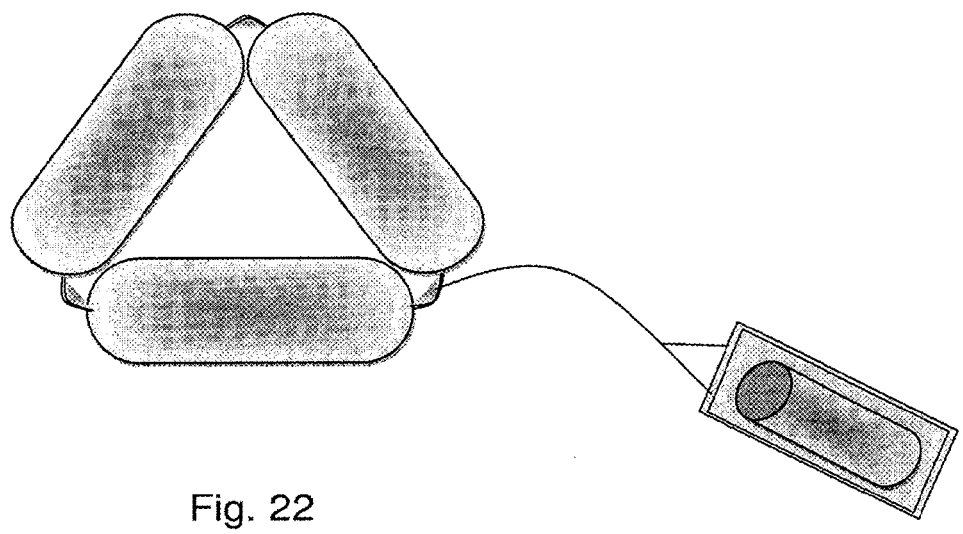
FIG. 22 and FIG. 23 depicts a gastric retentive element of a device of the invention having three compartments interconnected between them in their wet expanded form connected to a dosage form element through an external connecting link (thread or film) wherein said drug is encased in a film layer.
Figure 23:
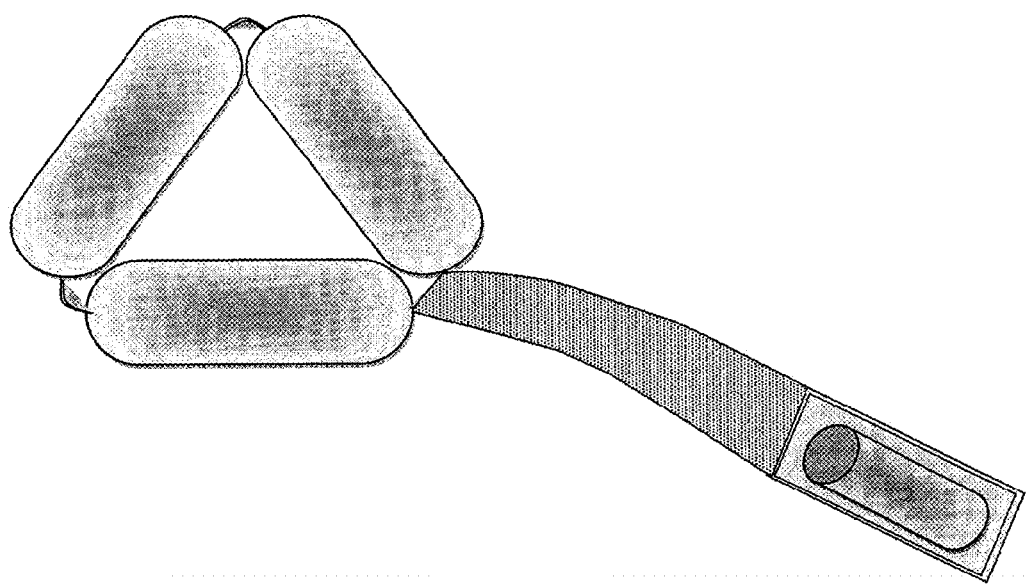
Figure 24:
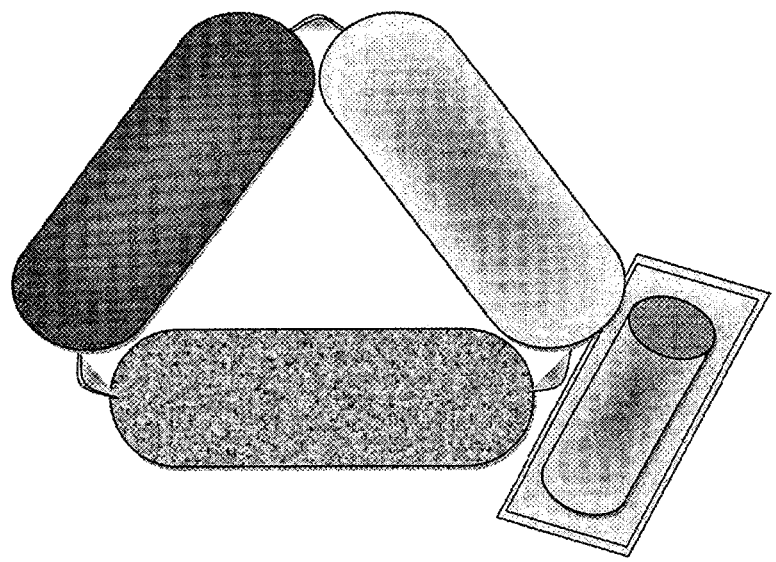
FIG. 24 depicts a gastric retentive element of a device of the invention having three compartments interconnected between them in their wet expanded form each one comprising a different compound capable of expanding said compartment, connected through a seam to a dosage form element wherein said drug is encased in a film layer.
Figure 25:
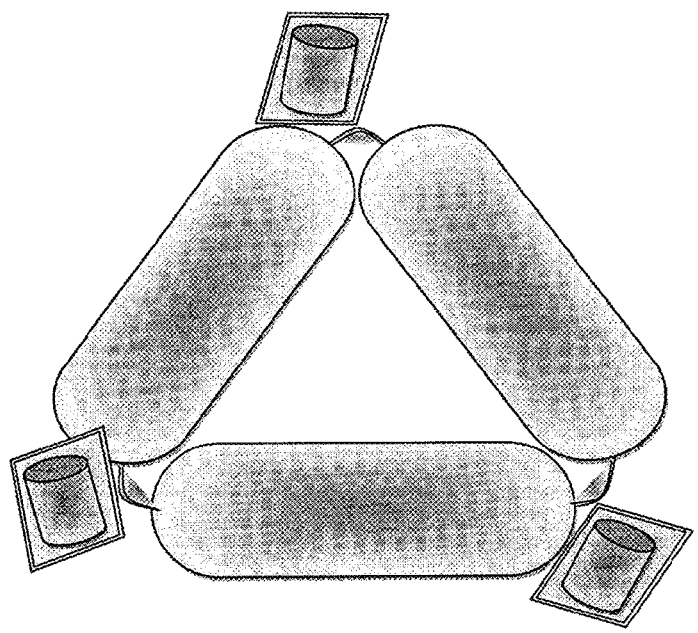
FIG. 25 depicts a gastric retentive element of a device of the invention having three compartments interconnected between them in their wet expanded form each one connected through a seam to a dosage form element wherein said drug is encased in a film layer.
Figure 26:
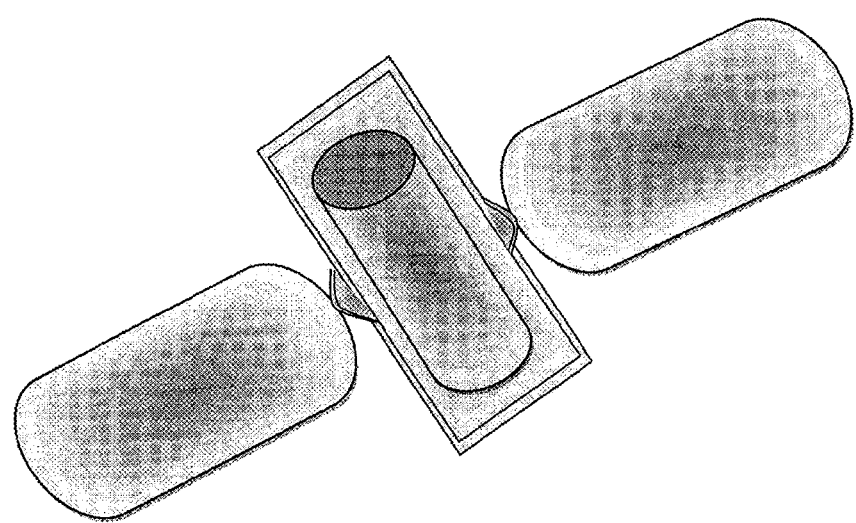
FIG. 26 depicts a device of the invention having two compartments in their wet expanded form connected through a seam to each side of a dosage form element wherein said drug is encased in a film layer.
Figure 27:
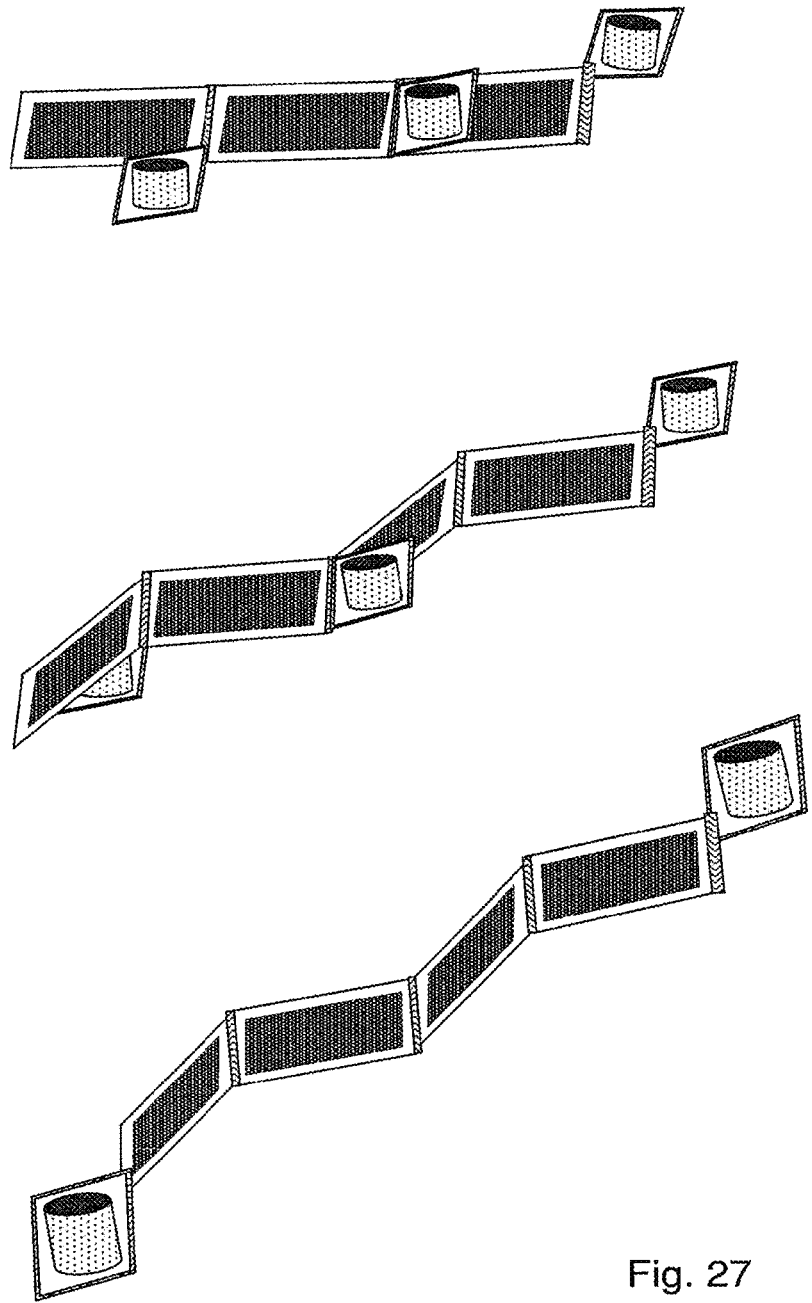
FIG. 27 depicts three embodiments of a device of the invention having three or four gastric retentive elements interconnected to each other through a seam and to two or three dosage form element wherein said drug is encased in a film layer.
Figure 28:
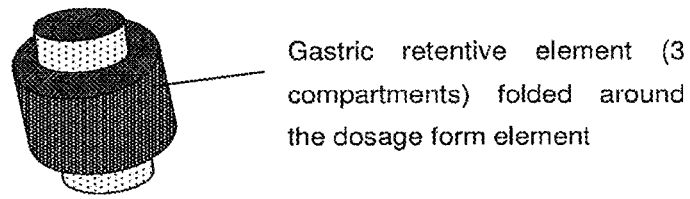
FIG. 28 depicts a device of the invention in a folded form showing the gastric retentive element in a film form rolled round the dosage form element.
Figure 29:
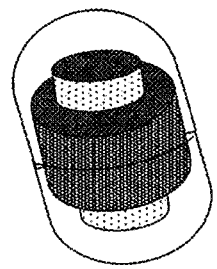
FIG. 29 depicts a device of the invention in a folded form showing the gastric retentive element in a film form rolled round the dosage form element all incased in a swallowable capsule.
Figure 30:
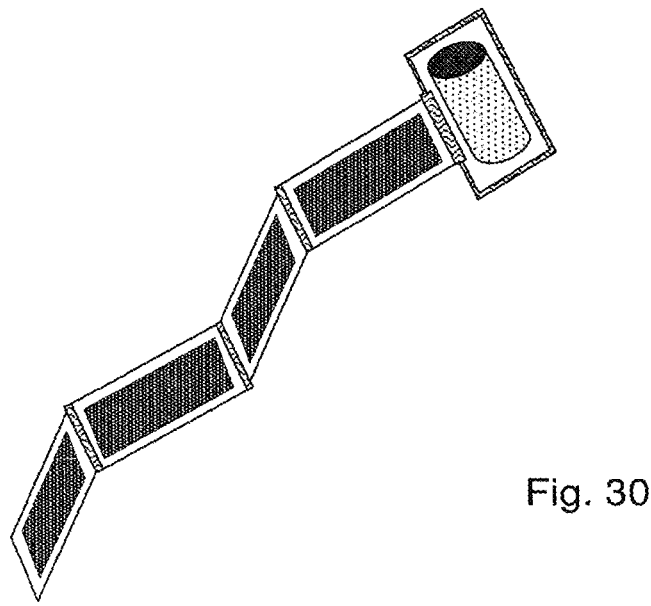
FIG. 30 depicts a device of the invention showing the gastric retentive element having four compartments in a dry non expanded form and a dosage form element connected through a seam on the external film layer of said element.
Figure 31:
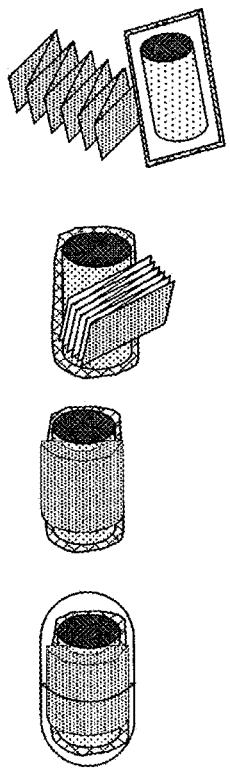
FIG. 31 depicts the method of folding a gastric retentive element of a device of the invention and rolling it around a dosage form element connected through a seam on the external film layer of said element.
Figure 32:
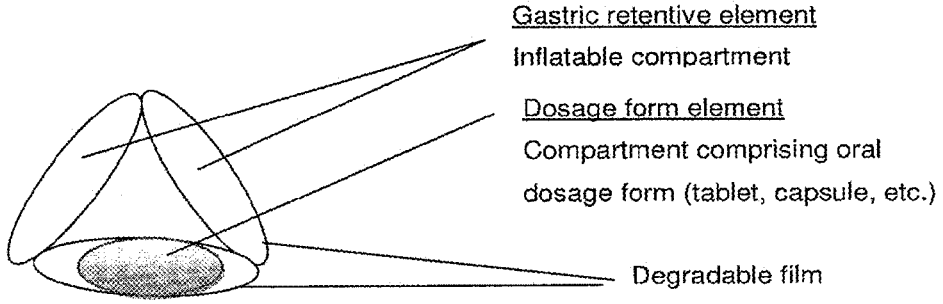
FIG. 32 depicts a device of the invention having two gastric retentive elements and a dosage from element comprising a tablet in a compartment. All compartments interconnected in a triangle form.
Figure 33:
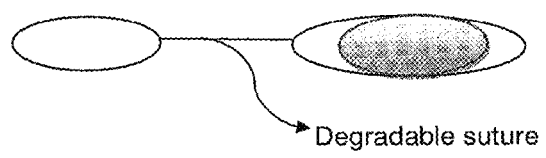
FIG. 33 depicts a device of the invention having a gastric retentive element of a single expandable compartment connected through a thread or suture to a dosage form element in a compartment having an external continuous film.
Figure 34:
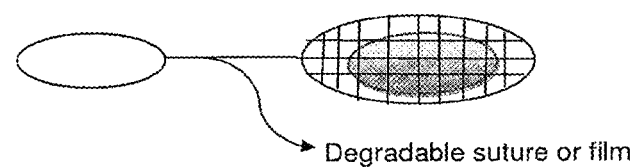
FIG. 34 depicts a device of the invention having a gastric retentive element of a single expandable compartment connected through a thread or suture to a dosage form element in a compartment having an external film in a net form.
Figure 35:
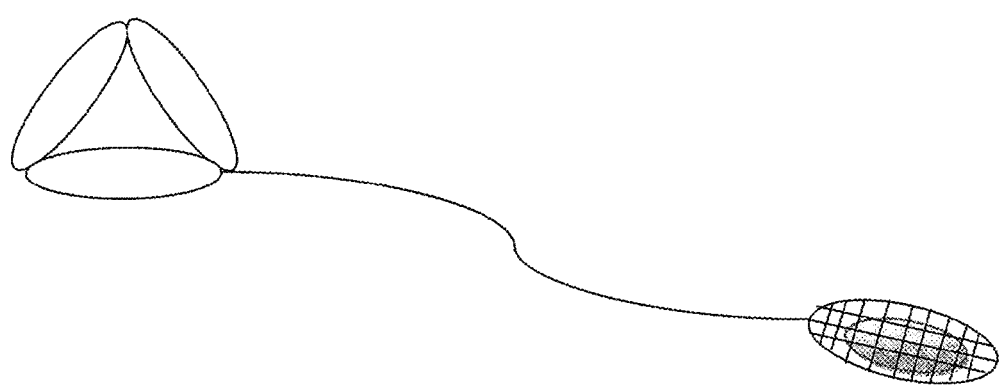
FIG. 35 depicts a device of the invention having a gastric retentive element of three expandable compartment connected to each other forming a triangle, said element is connected through a thread or suture to a dosage form element in a compartment having an external film in the form of a net.

The invention claimed is:

1. A folded expandable gastro-retentive system comprising
   (a) a folded gastric retentive element comprising at least one expandable compartment, said at least one expandable compartment comprising:
      walls formed by at least one external enterically biodegradable film, the walls having an inner surface and an outer surface, and having peripheral areas where the walls are joint together to form between said walls a space enclosed by the inner surface of the walls; and
      at least one gel-forming compound contained within said space and enclosed by the walls;
      the at least one gel-forming compound is enveloped by the walls to be within the space as a distinct element from the external enterically biodegradable film,
      wherein the external enterically biodegradable film and the at least one gel-forming compound do not together form a multi-layer film;
      wherein all gel-forming compound of the system is said at least one gel-forming compound within said space;
      the at least one gel-forming compound being capable of increasing the volume of each of the at least one expandable compartment from a volume defining an initial collapsed form to a larger volume defining an expanded form;
      such that when the folded expandable gastro-retentive system is swallowed:
         (i) the folded gastric retentive element is unfolded,
         (ii) said at least one gel-forming compound absorbs water,
         (iii) the volume of the gel-forming compound increases as it absorbs water such that the volume of the at least one compartment increases to define the expanded form, and
         (iv) the gastric retentive element adopts a structure of a ring, a rod or a polygonal shape, and
   (b) a dosage form element comprising at least one active agent;
      wherein said gastric retentive element and dosage form element are connected to each other.

2. The system according to claim 1,
   wherein the at least one active agent is in a slow release form or is a poorly soluble agent and
   wherein said gastric retentive element and dosage form element are externally connected to each other.

3. The system according to claim 1, wherein said dosage form element is enclosed in at least one external biodegradable film.

4. The system according to claim 3, wherein said biodegradable film provides prolonged or controlled release properties to said at least one active agent of said dosage from the gastric retentive element.

5. The system according to claim 1, being encased in a gastric degradable swallowable capsule.

6. The system according to claim 1, wherein said external biodegradable film has a thickness of less than 400 microns.

7. The system according to claim 1, wherein said film comprises at least one mechanical or chemically formed aperture.

8. The system according to claim 1, wherein said space of said at least one compartment has a total filling volume of at least 1 cm$^3$.

9. The system according to claim 1, wherein said space of said at least one compartment has a total filling volume of between about 1 cm$^3$ to about 50 cm$^3$.

10. The system according to claim 1, wherein upon reaching the stomach said external film of said at least one compartment allows for the penetration of liquid into said compartment, thereby at least partially increasing its volume and/or expanding its form.

11. The system according to claim 1, wherein said at least one active agent is in a controlled release formulation.

12. The system according to claim 1, wherein said at least one active agent has a gastric retention time of at least 8 h.

13. The system according to claim 1, wherein said at least one active agent has a gastric retention time of between about 8 h to about 48 h.

14. A method of gastrically delivering an active agent to a patient comprising: administering to said patient a system comprising
   (a) a folded gastric retentive element comprising at least one expandable compartment, said at least one expandable compartment comprising
      walls formed by at least one external enterically biodegradable film, the walls having an inner surface and an outer surface, and having a peripheral area where the walls are joint together to form between them a space enclosed by the inner surface of the walls; and
      at least one gel-forming compound contained within said space and enclosed by the walls;
      the at least one gel-forming compound is enveloped by the walls to be within the space as a distinct element from the external enterically biodegradable film,
      wherein the external enterically biodegradable film and the at least one gel-form ing compound do not together form a multi-layer film;
      wherein all gel-forming compound of the system is said at least one gel-forming compound within said space, the at least one gel-forming compound being capable of increasing the volume of each of the at least one expandable compartment from a volume defining an initial collapsed form to a larger volume defining an expanded form;

such that when the folded expandable gastro-retentive system is swallowed:
(i) the folded element is unfolded,
(ii) said at least one gel-forming compound absorbs water,
(ii) the volume of the gel-forming compound increases as it absorbs water such that the volume of the at least one compartment increases to define the expanded form and the gastric retentive element adopts a structure of a ring, a rod or a polygonal shape, and (b) a dosage form element comprising at least one active agent;

wherein said gastric retentive element and dosage form element are connected to each other.

15. The system according to claim 1, wherein said polygonal shape is selected from an octet, a triangle, a square, a pentagon, and a hexagon.

16. The system according to claim 1, wherein said at least one gel-forming compound is provided as a film of the at least one gel-forming compound.

17. The system according to claim 1, wherein the folded gastric retentive element comprises at least two expandable compartments.

18. The system according to claim 1, wherein gastric retentive element provides the system a stomach residence time between 1 hour and 30 days and the compartment loses its structure by gel shrinkage of the gel formed by the gel-forming material.

19. The system according to claim 18, wherein the at least one external enterically biodegradable film is enterically degradable to have its properties selected from at least one of tensile strength and/or elasticity degraded upon exposure to a biological environment in intestines.

20. The system according to claim 18, wherein the gel-forming material is a liquid or a powder.

21. A folded expandable gastro-retentive system comprising
(a) a folded gastric retentive element comprising at least one expandable compartment, said at least one expandable compartment comprising:
walls formed by at least one external enterically biodegradable film, the walls having an inner surface and an outer surface, and having peripheral areas where the walls are joint together to form between them a space enveloped by the inner surface of the walls; and
at least one gel-forming compound contained within said space and enveloped by the walls;
the at least one gel-forming compound is contained within the space as a distinct element from the external enterically biodegradable film,
wherein all gel-forming compound of the system is said at least one gel-forming compound within said space;
the at least one gel-forming compound being capable of increasing the volume of each of the at least one expandable compartment from a volume defining an initial collapsed form to a larger volume defining an expanded form;
wherein the external enterically biodegradable film and the at least one gel-forming compound do not together form a multi-layer film in the folded form and in the expanded form;
such that when the folded expandable gastro-retentive system is swallowed:
(i) the folded gastric retentive element is unfolded,
(ii) said at least one gel-forming compound absorbs water,
(iii) the volume of the gel-forming compound increases as it absorbs water such that the volume of the at least one compartment increases to define the expanded form, and
(iv) the gastric retentive element adopts a structure of a ring, a rod or a polygonal shape, and
(b) a dosage form element comprising at least one active agent;
wherein said gastric retentive element and dosage form element are connected to each other.

22. The system according to claim 1, wherein the at least one external enterically biodegradable film defines first and second opposed said walls to define first and second opposed said inner surfaces, respectively, wherein the first and second walls are joint together to form between said first and second walls the space enclosed by the inner surface of the first and second walls, the first wall being a top said external enterically biodegradable film and the second wall being a bottom said external enterically biodegradable film.

* * * * *